US012465750B2

(12) United States Patent
Obuchovsky et al.

(10) Patent No.: US 12,465,750 B2
(45) Date of Patent: Nov. 11, 2025

(54) DEVICES, SYSTEMS, AND METHODS FOR REMOVING AND REPLACING A SUBASSEMBLY OF AN ELECTRODE ASSEMBLY

(71) Applicant: NOVOCURE GMBH, Root (CH)

(72) Inventors: Stas Obuchovsky, Haifa (IL); Yoram Wasserman, Haifa (IL); David Shapiro, Haifa (IL)

(73) Assignee: NOVOCURE GMBH, Baar (CH)

( * ) Notice: Subject to any disclaimer, the term of this patent is extended or adjusted under 35 U.S.C. 154(b) by 0 days.

(21) Appl. No.: 18/622,143

(22) Filed: Mar. 29, 2024

(65) Prior Publication Data

US 2024/0325726 A1 Oct. 3, 2024

Related U.S. Application Data

(60) Provisional application No. 63/548,656, filed on Feb. 1, 2024, provisional application No. 63/493,561, filed on Mar. 31, 2023.

(51) Int. Cl.
*A61N 1/04* (2006.01)
*A61N 1/36* (2006.01)

(52) U.S. Cl.
CPC ....... *A61N 1/0408* (2013.01); *A61N 1/36002* (2017.08)

(58) Field of Classification Search
CPC ... A61N 1/0496; A61N 1/0476; A61N 1/0472
See application file for complete search history.

(56) References Cited

U.S. PATENT DOCUMENTS 4,779,630 A 10/1988 Scharnberg
5,450,845 A 9/1995 Axelgaard
5,733,324 A * 3/1998 Ferrari .................. A61N 1/046 607/152

FOREIGN PATENT DOCUMENTS

CN 108568029 A 9/2018
WO 2010/151875 A1 12/2010

OTHER PUBLICATIONS

International Search Report and Written Opinion for PCT/IB2024/053114, dated Jul. 5, 2024.

* cited by examiner

*Primary Examiner* — George R Evanisko
(74) *Attorney, Agent, or Firm* — Ballard Spahr LLP

(57) ABSTRACT

Apparatuses for use in applying TTFields are disclosed. An apparatus comprises an electrode subassembly including at least one electrode element having a skin-facing side and a skin-facing surface. The apparatus further includes a skin contact subassembly comprising a skin contact conductive adhesive or gel configured to contact skin of a subject. One of the electrode subassembly or the skin contact subassembly comprises an electrically conductive polymer layer, and the other of the electrode subassembly or the skin contact subassembly comprises a second conductive adhesive or gel. The electrically conductive polymer layer is disposed against, and removably coupled to, the second conductive adhesive or gel, thereby removably coupling the electrode subassembly to the skin contact subassembly so that the skin contact conductive adhesive or gel is electrically coupled to the at least one electrode element.

20 Claims, 14 Drawing Sheets

DEVICES, SYSTEMS, AND METHODS FOR REMOVING AND REPLACING A SUBASSEMBLY OF AN ELECTRODE ASSEMBLY

CROSS-REFERENCE TO RELATED APPLICATION

This application claims priority to and the benefit of the filing date of each of U.S. Provisional Patent Application Nos. 63/493,561, filed Mar. 31, 2023, and 63/548,656, filed Feb. 1, 2024, the entirety of each of which is hereby incorporated by reference herein.

BACKGROUND

Tumor Treating Fields (TTFields) therapy is a proven approach for treating tumors using alternating electric fields at frequencies between 50 KHz-1 MHz, such as 100-500 kHz. The alternating electric fields are induced by electrode assemblies (e.g., arrays of capacitively coupled electrodes, also called transducer arrays) placed on opposite sides of a target location in the subject's body. When an AC voltage is applied between opposing electrode assemblies, an AC current is coupled through the electrode assemblies and into the subject's body. And higher currents are strongly correlated with higher efficacy of treatment.

The electrode assemblies used during application of TTFields typically include an electrically conductive hydrogel layer that serves as a skin contact layer that adheres to the skin of the subject. The electrically conductive hydrogel typically has a shorter lifespan than the rest of the electrode assembly. For example, with use, the skin contact layer can degrade, for example, by collecting oil and dirt, thereby reducing effectiveness of the electrically conductive hydrogel layer. The hydrogel is typically integral to the electrode assembly. Thus, upon expiration or contamination of the hydrogel, the entire electrode assembly must be disposed of and replaced.

SUMMARY

Disclosed herein, in various aspects, are apparatuses and kits for applying TTFields.

In one aspect, an apparatus comprises an electrode subassembly having a skin-facing side and a skin-facing surface. The electrode subassembly comprises at least one electrode element having a skin-facing side and a skin-facing surface. The apparatus further comprises a skin contact subassembly comprising a skin contact conductive adhesive or gel configured to contact skin of a subject. One of the electrode subassembly or the skin contact subassembly comprises an electrically conductive polymer layer, and the other of the electrode subassembly or the skin contact subassembly comprises a conductive adhesive or gel layer. The skin contact subassembly is removably coupled to the electrode subassembly by adhesion between the electrically conductive polymer layer and the conductive adhesive or gel layer. The skin contact conductive adhesive or gel is electrically coupled to the at least one electrode element when the skin contact subassembly is disposed against the skin-facing surface of the electrode subassembly.

In one aspect, a kit comprises an electrode subassembly. The electrode subassembly comprises at least one electrode element having a skin-facing side and a skin-facing surface and a non-adhesive electrically conductive polymer layer on the skin-facing side of the at least one electrode element. The non-adhesive electrically conductive polymer layer has a skin-facing surface which defines a skin-facing surface of the electrode subassembly. The kit further comprises a plurality of skin contact subassemblies, each skin contact subassembly configured to couple to the electrode subassembly as a removable unit. Each skin contact subassembly comprises a skin contact conductive adhesive or gel configured to contact skin of a subject. When the skin contact subassembly is disposed against the non-adhesive electrically conductive polymer layer of the electrode subassembly, the skin contact conductive adhesive or gel of the skin contact subassembly is configured to electrically couple to the at least one electrode element.

In one aspect, a method comprises using an apparatus, wherein the apparatus comprises an electrode subassembly having a skin-facing side and a skin-facing surface. The electrode subassembly comprises at least one electrode element having a skin-facing side and a skin-facing surface. The apparatus further comprises a skin contact subassembly comprising a skin contact conductive adhesive or gel configured to contact skin of a subject. One of the electrode subassembly or the skin contact subassembly comprises an electrically conductive polymer layer, and the other of the electrode subassembly or the skin contact subassembly comprises a conductive adhesive or gel layer. The skin contact subassembly is removably coupled to the electrode subassembly by adhesion between the electrically conductive polymer layer and the conductive adhesive or gel layer. The skin contact conductive adhesive or gel is electrically coupled to the at least one electrode element when the skin contact subassembly is disposed against the skin-facing surface of the electrode subassembly. The method further comprises removing the skin contact subassembly from the electrode subassembly.

In one aspect, an apparatus comprises an electrode subassembly comprising at least one electrode element having a skin-facing side and a skin-facing surface. The electrode subassembly further comprises an electrically conductive polymer layer on the skin-facing side of the at least one electrode element. The electrically conductive polymer layer has a skin-facing surface which defines a skin-facing surface of the electrode subassembly. The apparatus further comprises a skin contact subassembly removably coupled to the electrode subassembly. The skin contact subassembly comprises a skin contact conductive adhesive or gel configured to contact skin of a subject. The skin contact conductive adhesive or gel is electrically coupled to the at least one electrode element when the skin contact subassembly is disposed against the skin-facing surface of the electrically conductive polymer layer of the electrode subassembly.

In one aspect, a kit comprises an electrode subassembly comprising at least one electrode element having a skin-facing side and a skin-facing surface. The electrode subassembly further comprises an electrically conductive polymer layer on the skin-facing side of the at least one electrode element. The electrically conductive polymer layer has a skin-facing surface which defines a skin-facing surface of the electrode subassembly. The kit further comprises a plurality of skin contact subassemblies. Each skin contact subassembly is configured to couple to the electrode subassembly as a removable unit. Each skin contact subassembly comprises a skin contact conductive adhesive or gel configured to contact skin of a subject. When the skin contact subassembly is disposed against the electrically conductive polymer layer of the electrode subassembly, the skin contact conductive adhesive or gel of the skin contact subassembly is configured to electrically couple to the at least one electrode element.

In one aspect, an apparatus comprises an electrode subassembly comprising at least one electrode element having a skin-facing side and a skin-facing surface. The electrode subassembly further comprises a first conductive adhesive or gel on the skin-facing side of the at least one electrode element. The first conductive adhesive or gel has a skin-facing surface which defines a skin-facing surface of the electrode subassembly. The apparatus further comprises a skin contact subassembly removably coupled to the electrode subassembly. The skin contact subassembly comprises an electrically conductive polymer layer configured to removably couple to the skin-facing surface of the electrode subassembly. The skin contact subassembly further comprises a skin contact conductive adhesive or gel configured to contact skin of a subject. The skin contact conductive adhesive or gel is electrically coupled to the at least one electrode element when the conductive polymer layer of the skin contact subassembly is disposed against the skin-facing surface of the electrode subassembly.

In one aspect, a kit comprises an electrode subassembly comprising at least one electrode element having a skin-facing side and a skin-facing surface. The electrode subassembly further comprises a first conductive adhesive or gel on the skin-facing side of the at least one electrode element. The first conductive adhesive or gel has a skin-facing surface which defines a skin-facing surface of the electrode subassembly. The kit further comprises a plurality of skin contact subassemblies. Each skin contact subassembly is configured to couple to the electrode subassembly as a removable unit. Each skin contact subassembly comprises an electrically conductive polymer layer configured to be removably coupled to the skin-facing surface of the electrode subassembly and a skin contact conductive adhesive or gel configured to contact skin of a subject. When the electrically conductive polymer layer of the skin contact subassembly is disposed against the skin-facing surface of the electrode subassembly, the skin contact conductive adhesive or gel of the skin contact subassembly is electrically coupled to the at least one electrode element.

In one aspect, an apparatus comprises an electrode subassembly including at least one electrode element having a skin-facing side and a skin-facing surface. The apparatus further includes a skin contact subassembly comprising a skin contact conductive adhesive or gel configured to contact skin of a subject. One of the electrode subassembly or the skin contact subassembly comprises an electrically conductive polymer layer, and the other of the electrode subassembly or the skin contact subassembly comprises a second conductive adhesive or gel. The electrically conductive polymer layer is disposed against, and removably coupled to, the second conductive adhesive or gel, thereby removably coupling the electrode subassembly to the skin contact subassembly so that the skin contact conductive adhesive or gel is electrically coupled to the at least one electrode element.

In one aspect, an apparatus comprise an electrode subassembly comprising at least one electrode element having a skin-facing side and a skin-facing surface. The apparatus further comprises a skin contact subassembly comprising a skin contact conductive adhesive or gel. The skin contact conductive adhesive or gel is electrically coupled to the at least one electrode element and configured to contact skin of a subject. One of the electrode subassembly or the skin contact subassembly comprises an electrically conductive polymer layer. The skin contact subassembly is removably coupled to the electrode subassembly by adhesion between the electrically conductive polymer layer and a conductive adhesive layer of the other of the electrode subassembly or the skin contact subassembly.

Systems and methods for using the disclosed apparatuses and kits (e.g., treatment assemblies) are also disclosed.

BRIEF DESCRIPTION OF THE DRAWINGS

Various embodiments are described in detail below with reference to the accompanying drawings, wherein like reference numerals represent like elements.

DETAILED DESCRIPTION

This application describes exemplary electrode assemblies that can be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise. Thus, it is contemplated that disclosure of a singular form of an element can provide support for embodiments in which only a single such element is provided, as well as support for embodiments in which a plurality of such elements are provided.

As used herein, the term "conductive adhesive or gel" should be understood to mean "conductive adhesive or conductive gel." Further, the term "conductive gel" should be understood to include hydrogel.

As used herein, the term "front" refers to a skin-facing side of an element, and "rear" refers to an outwardly facing side opposite the skin-facing side of an element.

Existing electrode assemblies for providing TTFields are unitarily constructed as an assembly with one or more electrode elements and a skin contact layer. As noted above, the whole construct needs to be replaced once the skin contact layer has been contaminated or has degraded. Disclosed herein are electrode assemblies that permit replacement of the skin contact layer and subsequent reuse of the electrode assembly (i.e. a 2-part array comprising an electrode subassembly and a skin contact subassembly).

Figure 1:
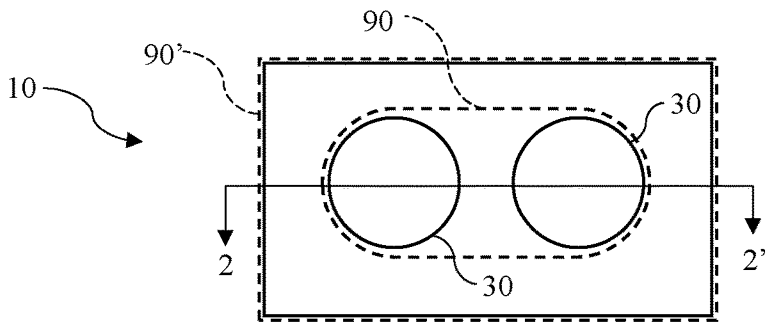
FIG. 1 is a schematic top view representation of an exemplary treatment assembly as disclosed herein.
Figure 2:
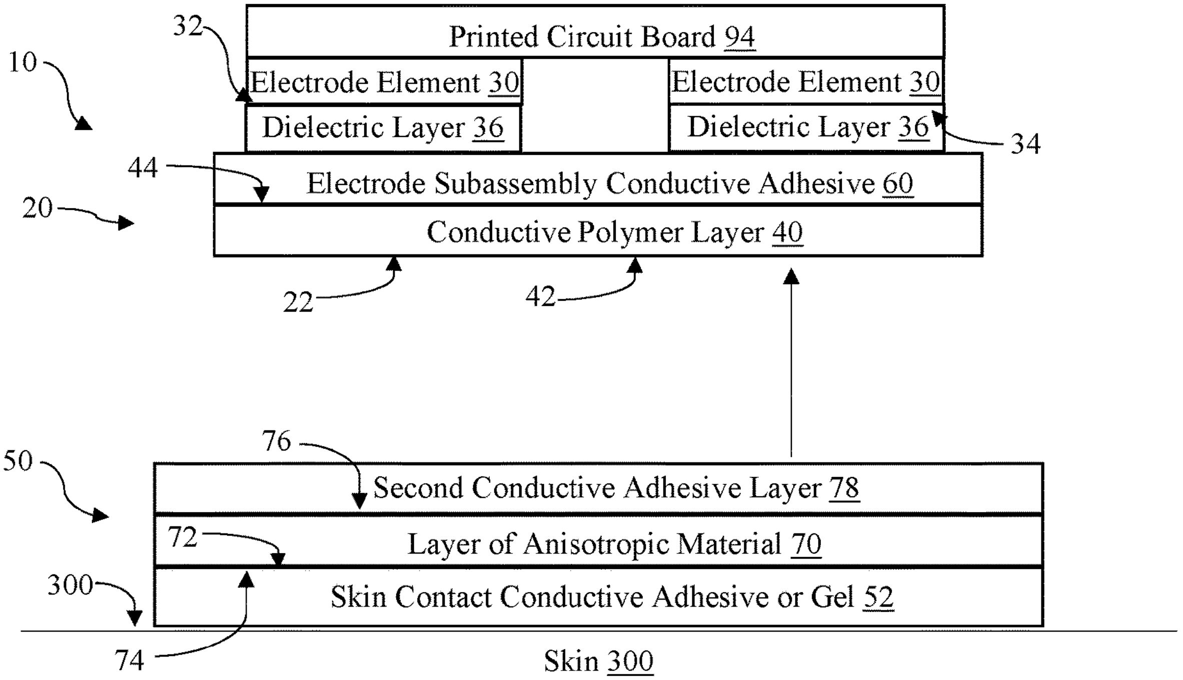
FIGS. 2-10 are schematic cross-sectional representations of exemplary treatment assemblies as disclosed herein, taken in the plane 2-2' of FIG. 1, according to various non-limiting embodiments.

FIG. 1 illustrates a top schematic view of an apparatus 10 for providing TTFields and shows two electrode elements 30 (although the apparatus could have one, two or more than two electrode elements 30). In some optional aspects, the apparatus 10 can comprise a plurality of electrode elements 30. In these aspects, the electrode elements 30 can be wired together (e.g., using wires, or traces on a printed circuit board 94 that can optionally be a flex circuit, etc.). As discussed further herein, the apparatus 10 can have an operative conductive area. For example, as shown in FIG. 1, the operative conductive area 90 can be defined by an outer perimeter that surrounds every electrode of the at least one electrode (e.g., an areal footprint of the at least one electrode element). Also discussed herein, in alternative aspects in which the apparatus comprises a layer of anisotropic conductive material 70 (e.g., FIG. 2), the operative conductive area 90' can be defined by the outer perimeter of the anisotropic material. Referring also to FIG. 2, showing a schematic cross-sectional representation of the apparatus 10, taken in the plane 2-2', the apparatus 10 can comprise an electrode subassembly 20, the electrode subassembly 20 comprising at least one electrode element 30 having a skin-facing side 32 and a skin-facing surface 34. The electrode subassembly 20 can further comprise a polymer layer on the skin-facing side 32 of the at least one electrode element 30, wherein the polymer layer is electrically conductive and referred to herein as electrically conductive polymer layer 40, even though the polymer per se may not be conductive. The electrically conductive polymer layer 40 can have a skin-facing surface 42 that defines a skin-facing surface 22 of the electrode subassembly 20. In some embodiments, the electrically conductive polymer layer 40 is a non-adhesive electrically conductive polymer layer.

Figure 3:
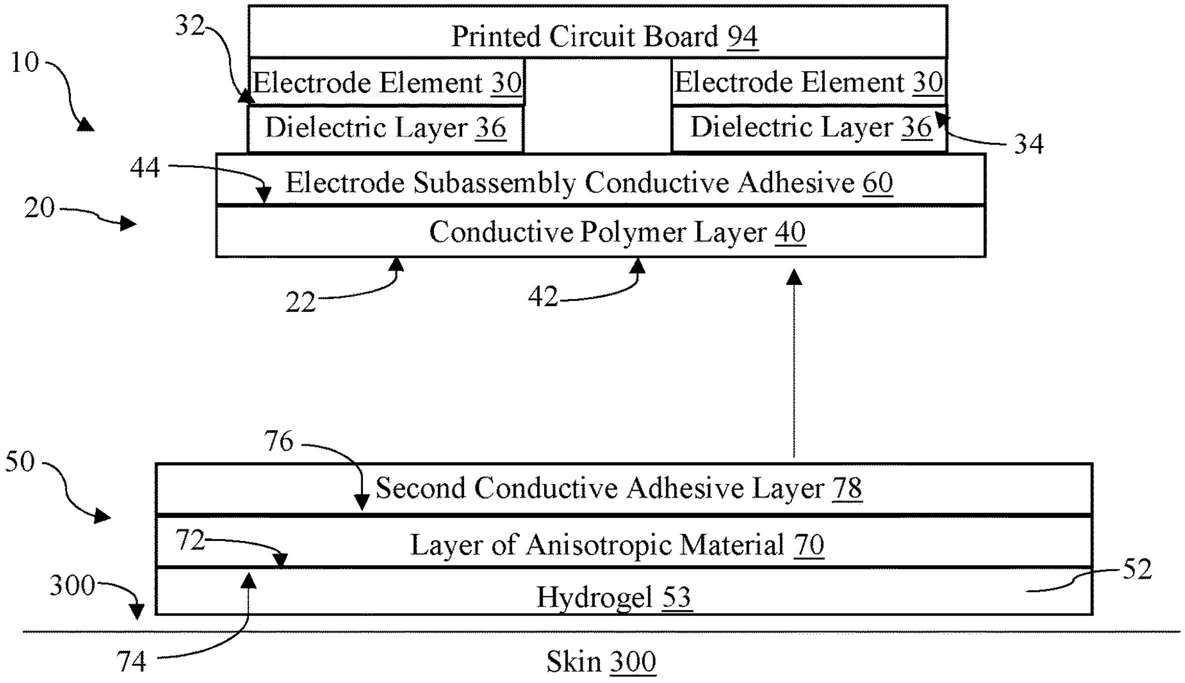

The apparatus 10 can further comprise a skin contact subassembly 50 removably coupled to the electrode subassembly 20. The skin contact subassembly 50 can comprise a skin contact conductive adhesive or gel 52 configured to contact skin 300 of a subject (e.g., FIGS. 2 and 4). Generally herein, the skin-facing surface of the skin contact conductive adhesive or gel 52 defines a skin-facing surface of the skin contact subassembly 50. The skin contact conductive adhesive or gel 52 can be electrically coupled to the at least one electrode element 30 when the skin contact subassembly 50 is disposed against the skin-facing surface of the electrically conductive polymer layer 40 of the electrode subassembly 20. In exemplary, optional aspects, and as illustrated in FIGS. 3 and 5, the skin contact conductive adhesive or gel 52 can comprise hydrogel 53. For example, FIG. 3 illustrates a similar embodiment to that shown in FIG. 2 (and with the same labelling scheme) wherein the skin contact conductive adhesive or gel is shown as hydrogel 53).

In some aspects, the electrically conductive polymer layer 40 of the electrode subassembly 20 can be a non-adhesive electrically conductive polymer layer. In some aspects, the electrically conductive polymer layer 40 of the electrode subassembly 20 can comprise a rubber or elastomer. In some exemplary aspects, the electrically conductive polymer layer 40 of the electrode subassembly 20 can comprise an adhesive or sealant. In some aspects, the electrically conductive polymer layer of the electrode subassembly can comprise a silicone polymer. In some aspects, the electrically conductive polymer layer of the electrode subassembly can comprise a polydimethylsiloxane (PDMS). In various aspects, the electrically conductive polymer layer of the electrode subassembly can comprise, for example, and without limitation, one or more of silicone rubber, silicone elastomer, natural rubber, poly cis-isoprene, polyisobutylene, polychloroprene, cis-polybutadiene, styrene-butadiene polymer, styrene-acrylonitrile-butadiene polymer, polyurethane, polymer of ethylene propylene diene monomer (EPDM), acrylic ethylene copolymer (AEM) polymers, ethylene-vinyl acetate (EVA) polymer, fluoropolymer, and perfluoropolymer. In some aspects, the electrically conductive polymer layer 40 of the electrode subassembly 20 can comprise polyetherimide, polyetherketone, polyethersulfone, polyether ether ketone, or polyaryl ether ketone.

In some aspects, the electrically conductive polymer layer 40 of the electrode subassembly 20 can comprise a composite material having conductive particles dispersed therethrough. For example, the conductive particles can comprise carbon. In exemplary aspects, the conductive particles can comprise one or more of: graphite powder, carbon flakes, carbon fibers, carbon granules, carbon nanotubes, carbon nanowires, carbon black powder, or carbon microcoils, and the like. In some aspects, the conductive particles can comprise metal. In exemplary aspects, the composite material can comprise polymer (e.g., a silicone polymer) with conductive particles dispersed therethrough. As used herein, a conductive species, in some embodiments, can optionally refer to a composite material comprising the species with conductive particles dispersed therethrough.

The electrically conductive polymer layer 40 of the electrode subassembly 20 can have an outwardly facing surface 44 that faces the at least one electrode 30. The electrode subassembly 20 can further comprise an electrode subassembly conductive adhesive or gel layer 60 disposed against the outwardly facing surface 44 of the electrically conductive polymer layer 40.

In some exemplary aspects, the electrode subassembly 20 can further comprise a dielectric layer 36 between the at least one electrode element 30 and the electrically conductive polymer layer 40 of the electrode subassembly 20. In exemplary aspects in which the electrode subassembly 20 comprises an electrode subassembly conductive adhesive or gel layer 60, the dielectric layer 36 can be positioned between the at least one electrode element 30 and the electrode subassembly conductive adhesive or gel layer 60. In some exemplary aspects, the dielectric layer 36 can be positioned in front of, and in contact with, the at least one electrode element 30.

Figure 10:
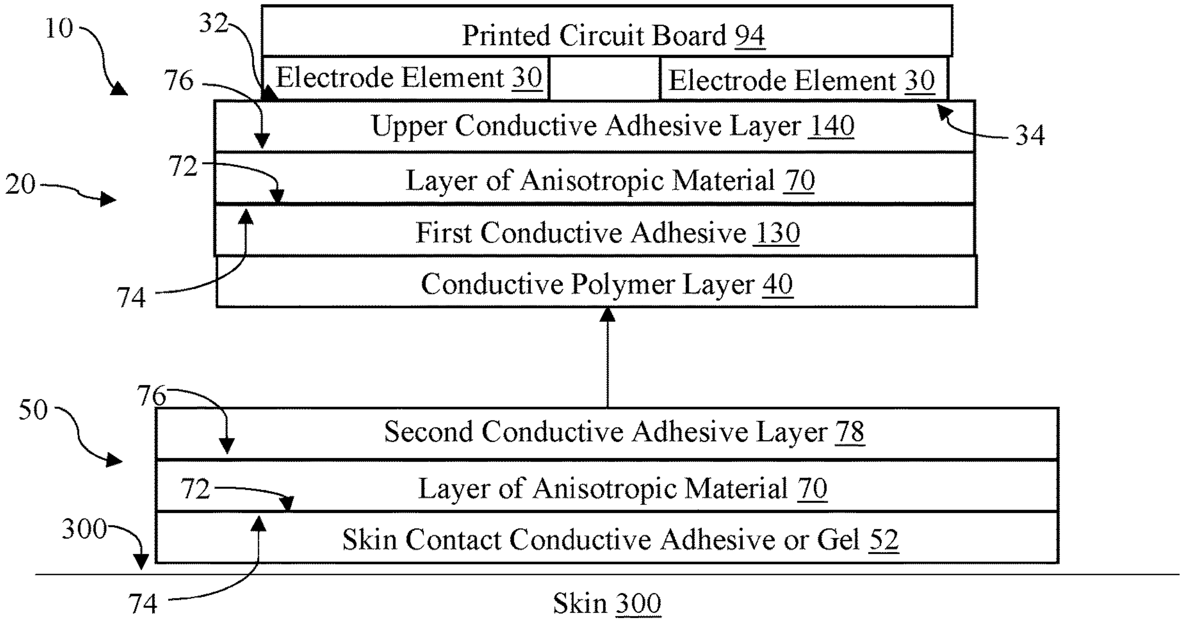

In some aspects, the dielectric layer 36 can comprise a ceramic. In some aspects, the dielectric layer 36 can comprise a dielectric polymer. In exemplary aspects the dielectric layer 36 can have a dielectric constant greater than 10 or greater than 20. Although shown in the Figures as separate discrete (discontinuous) layers on the surface of each electrode, in some aspects the dielectric layer 36 may be a single (continuous) layer covering a plurality of electrode elements or covering all of the electrode elements. In some aspects, and with reference to FIG. 10, the electrode subassembly 20 does not include a dielectric layer 36.

Figure 9:
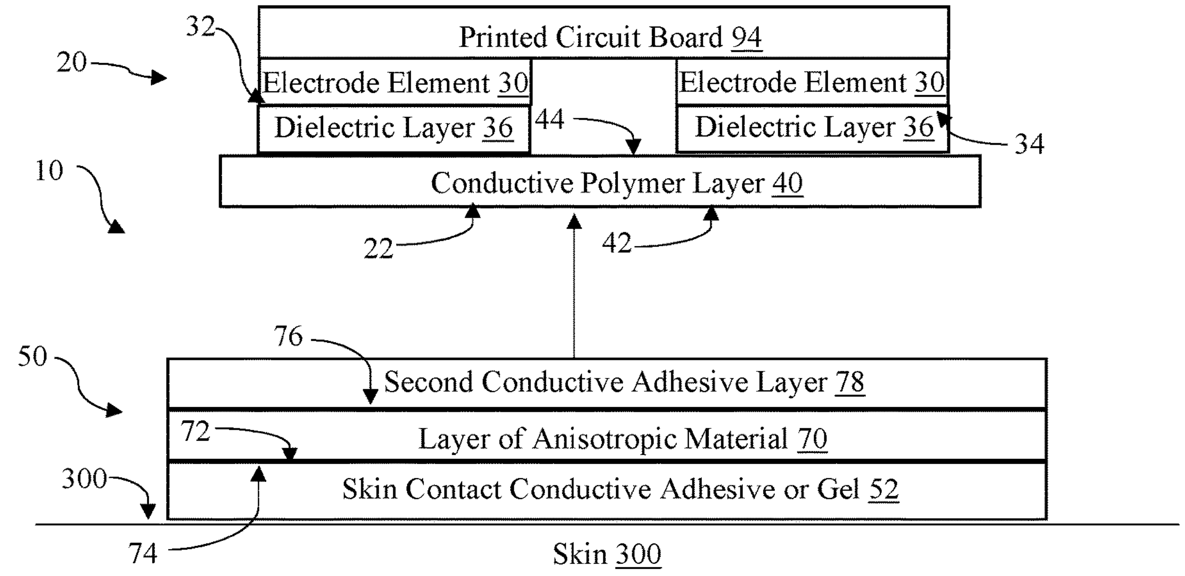

Optionally, in further aspects, and with reference to FIG. 9, the electrode subassembly conductive adhesive 60 can be omitted. For example, in some aspects, conductive polymer 40 (e.g., conductive silicone rubber) can be deposited directly (e.g., deposited from solution) onto the dielectric layer 36 (or directly on the electrode element(s) 30 where the dielectric layer is omitted), thereby establishing a stable interface between the electrically conductive polymer 40 and the dielectric layer 36 or electrode element(s) 30 without the need for additional adhesive (for example, an interface for which the conductive polymer 40 covers the whole surface of the dielectric layer 36, is mechanically stable (no detachments), and has a low contact resistance). Optionally, in these aspects, it is contemplated that the dielectric layer 36 can comprise ceramic material as further disclosed herein.

In some aspects, the apparatus 10 does not comprise (i.e. is free of) an additional adhesive (such as a structural adhesive) between the skin contact subassembly 50 and the electrically conductive polymer layer 40 of the electrode subassembly 20. For example, the electrically conductive polymer layer 40 of the electrode subassembly 20 and the skin contact subassembly 50 can be removably coupled by a physical, non-chemical adhesion. The electrically conductive polymer layer 40 of the electrode subassembly 20 and the skin contact subassembly 50 can be removably coupled by a Van der Waals attractive force. In some aspects, the weak Van der Waals attractive force may be supplemented. For example, the weak Van der Waals attractive force may be supplemented by an added attractive force around the perimeter, such as, for example, the positioning of one or more pairs of magnets (i.e. one of the pair on the electrode subassembly and the other of the pair on the skin contact subassembly); or a fastener, such as, for example, a hook and/or loop fastener (i.e. one of the hook or loop material on the electrode subassembly and the other of the hook or loop material on the skin contact subassembly).

In some aspects, the skin facing surface 42 of the electrically conductive polymer layer 40 of the electrode subassembly 20 can be smooth. In some optional aspects, the electrically conductive polymer layer 40 of the electrode subassembly 20 is not tacky.

In some aspects, and as shown in FIGS. 2-10 and 16-17, the skin contact subassembly 50 can optionally further comprise a layer of anisotropic conductive material 70 having a skin-facing side 72 with a skin-facing surface 74 and an opposing outwardly facing surface 76. The layer of anisotropic conductive material 70 can be disposed in contact with the skin contact conductive adhesive or gel 52. The at least one electrode element 30 can be in electrical contact with the outwardly facing surface 76 of the layer of anisotropic conductive material 70 when the electrode subassembly is in contact with the skin contact subassembly.

In some optional aspects, the skin contact conductive adhesive or gel 52 can comprise a conductive adhesive composite (described further herein). The conductive adhesive composite can comprise conductive particles dispersed therethrough. For example, the conductive particles can comprise carbon. In exemplary aspects, the conductive particles can comprise one or more of: graphite powder, carbon flakes, carbon fibers, carbon granules, carbon nanotubes, carbon nanowires, carbon black powder, or carbon microcoils. In some aspects, the conductive particles can comprise metal.

In exemplary aspects, as illustrated in FIGS. 2-10 and 16-17, the skin contact subassembly 50 can comprise a three-layer unit comprising the skin contact conductive adhesive or gel 52 (or hydrogel 53), a layer of anisotropic conductive material 70 (described further herein), and a second conductive adhesive or gel layer 78. In some aspects, the three-layer unit can further comprise an edge sealing non-conductive border such as a strip of tape that covers the perimeter edge of the three layers and, optionally adheres to the top and bottom surface of the three layer unit. The layer of anisotropic conductive material 70 can have a skin facing side 72 with a skin facing surface 74 and an opposing outwardly facing surface 76. The skin facing surface 74 of the layer of anisotropic conductive material 70 can be in contact with the skin contact conductive adhesive or gel 52. Optionally, the skin contact conductive adhesive or gel 52 can comprise hydrogel 53 (e.g., FIGS. 3 and 5). The outwardly facing surface 76 of the layer of anisotropic conductive material 70 can be in contact with the second conductive adhesive or gel layer 78. In still further optional aspects, the skin contact subassembly 50 can further comprise an additional skin-side conductive adhesive or gel between the layer of anisotropic conductive material 70 and the skin contact conductive adhesive or gel 52 (e.g., optionally, one of the layers can be hydrogel 53). For example, the additional skin-side conductive adhesive or gel may be a conductive adhesive composite and the skin contact conductive adhesive or gel may be a hydrogel.

Figure 4:
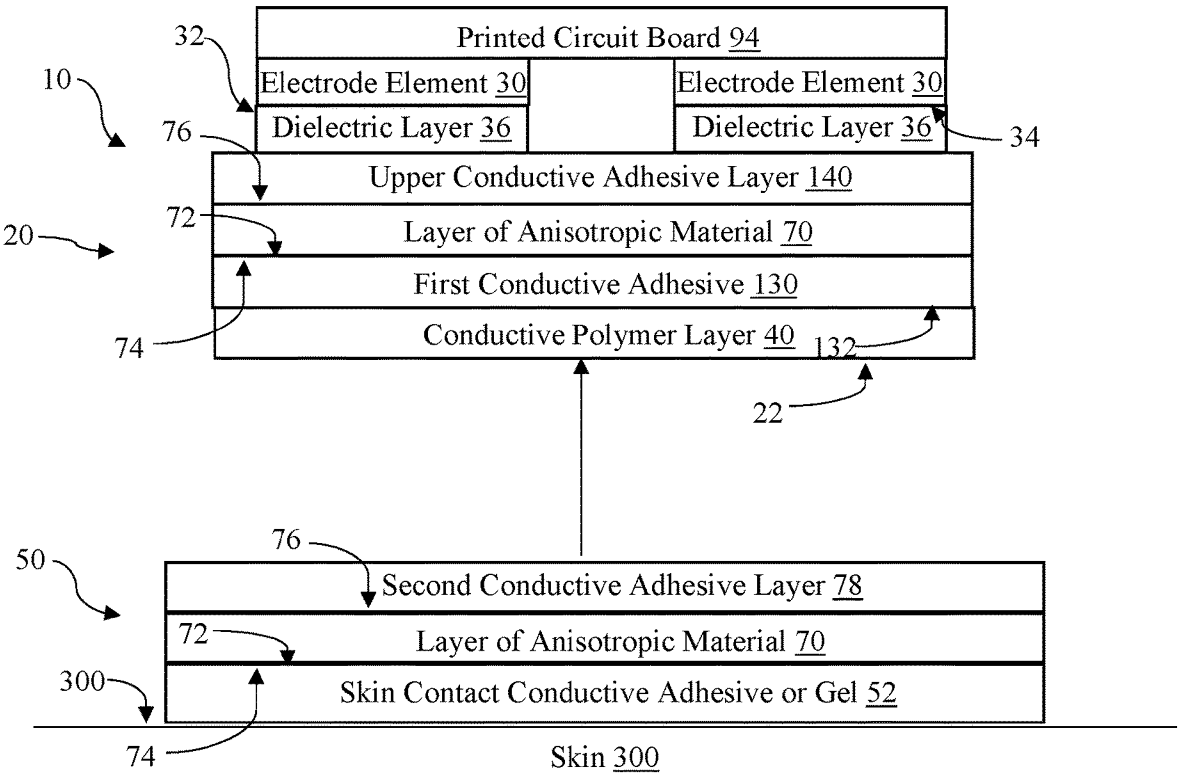
Figure 5:
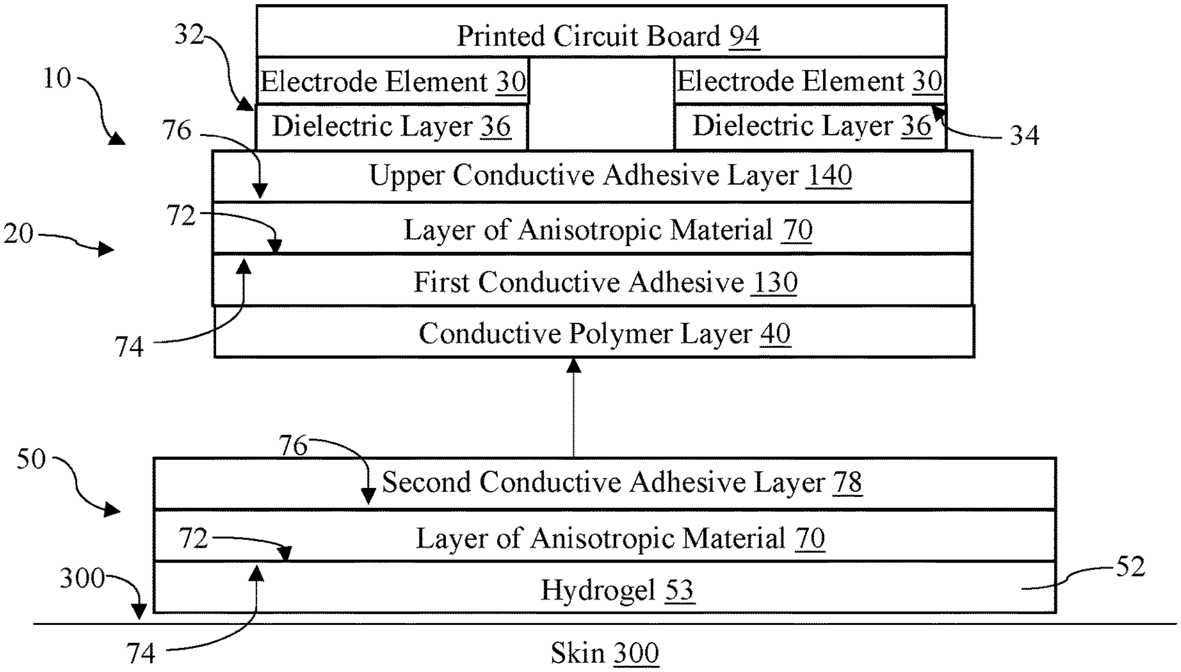

Referring to FIGS. 4-5 (and also shown in FIGS. 6-8, 10, 15 and 17), the electrode subassembly 20 can comprise a three-layer unit comprising the first conductive adhesive or gel 130, a layer of anisotropic conductive material 70, and an upper conductive adhesive or gel 140. The layer of anisotropic conductive material 70 can have a skin facing side 72 with a skin facing surface 74 and an opposing outwardly facing surface 76. The skin facing surface 74 of the layer of anisotropic conductive material 70 can be in contact with the first conductive adhesive or gel 130, and the outwardly facing surface 76 of the layer of anisotropic conductive material 70 can be in contact with the upper conductive adhesive or gel 140.

In some aspects, each of the electrode subassembly 20 and the skin contact subassembly 50 can comprise a layer of anisotropic conductive material 70 (see, for example, FIGS. 4-8, 10 and 17).

Figure 6:
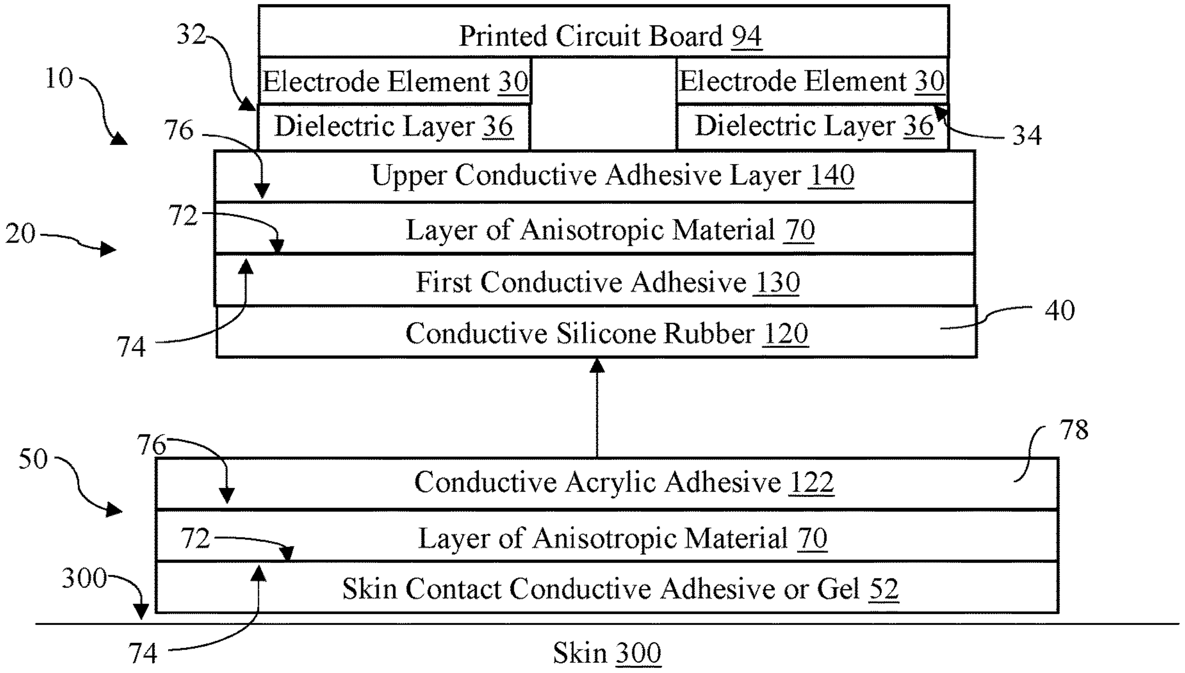
Figure 7:
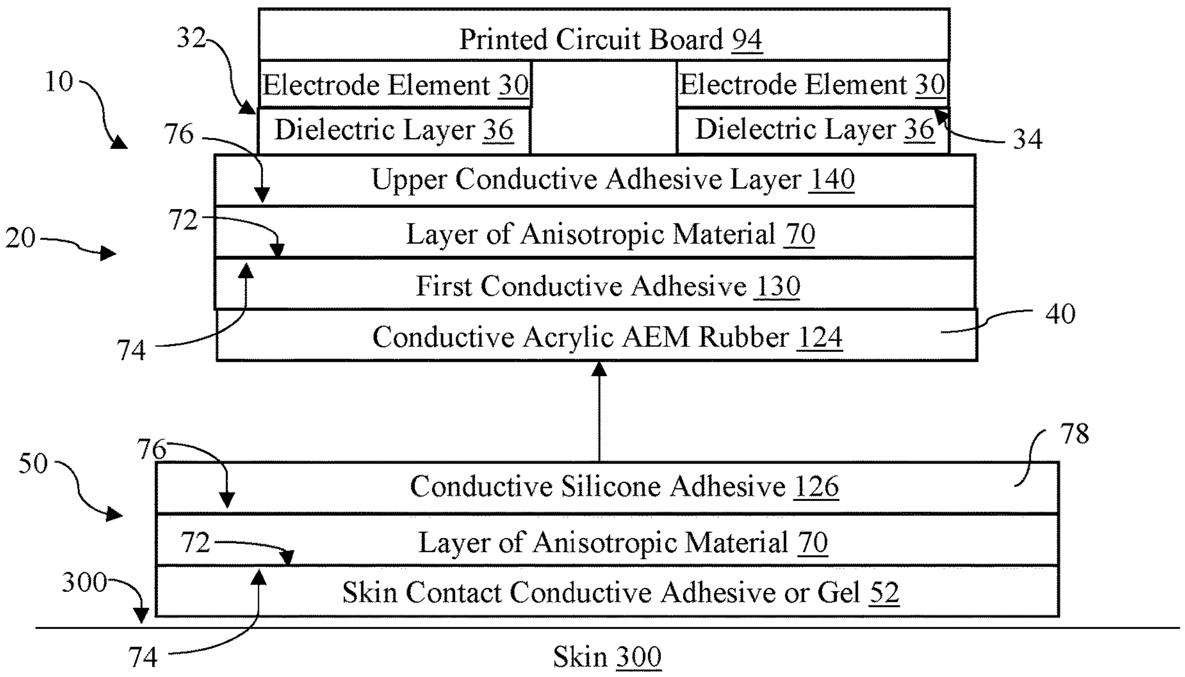
Figure 8:
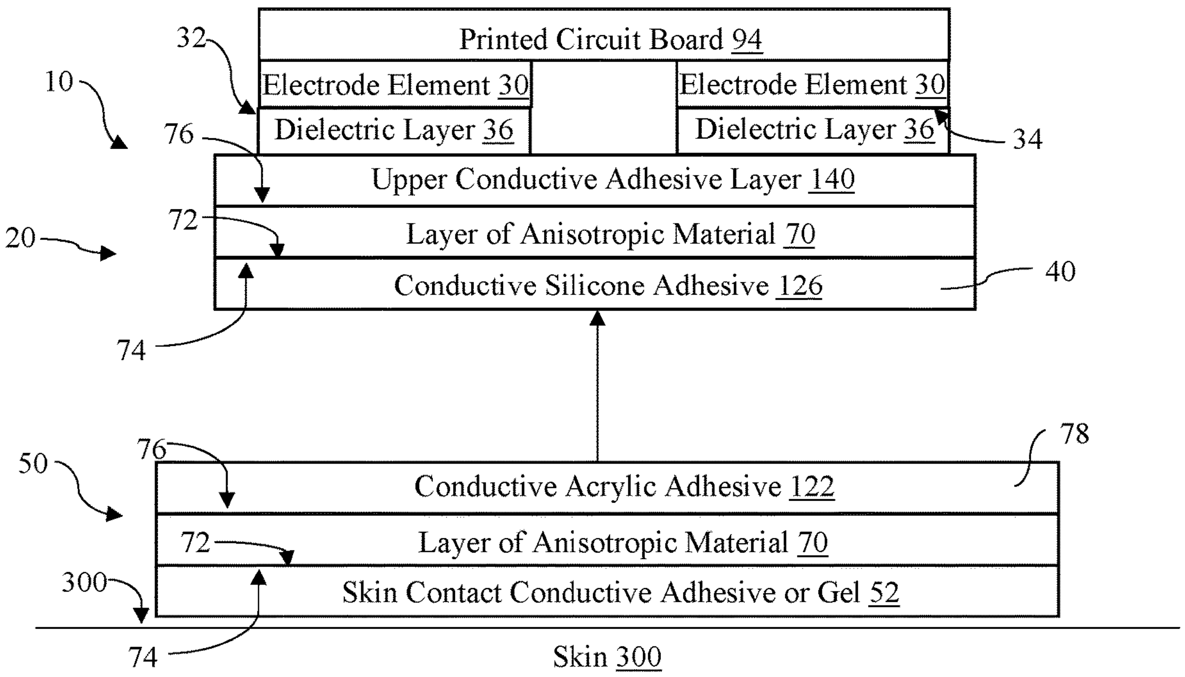

In some exemplary embodiments, and with reference to FIG. 6, the electrically conductive polymer layer 40 of the electrode subassembly 20 can comprise conductive silicone rubber 120 (e.g., silicone rubber having conductive particles dispersed therethrough), and the second conductive adhesive or gel layer 78 can comprise conductive acrylic adhesive 122 (e.g., acrylic adhesive having conductive particles dispersed therethrough). In other exemplary embodiments, and with reference to FIG. 7, the electrically conductive polymer layer 40 of the electrode subassembly 20 can comprise conductive acrylic AEM rubber 124, and the second conductive adhesive or gel layer 78 can comprise conductive silicone adhesive 126. In additional exemplary embodiments, and with reference to FIG. 8, the electrically conductive polymer layer 40 of the electrode subassembly 20 can comprise conductive silicone adhesive 126, and the second conductive adhesive or gel layer 78 can comprise conductive acrylic adhesive 122, or vice-versa.

In some aspects, the skin contact subassembly 50 can comprise acrylic adhesive. For example, in some aspects, the second conductive adhesive or gel layer 78 in contact with the electrically conductive polymer layer 40 of the electrode subassembly 20 can comprise acrylic adhesive. Moreover, in some aspects, the skin contact conductive adhesive or gel 52 can comprise acrylic adhesive.

A method of using the apparatus 10 can comprise removing the skin contact subassembly 50 from the electrically conductive polymer layer 40 of the electrode subassembly 20. For example, the skin contact subassembly 50 that is removed can be a used, or otherwise soiled, skin contact subassembly 50. A new skin contact subassembly 50 can be positioned against the electrically conductive polymer layer 40 of the electrode subassembly 20 so that the new skin contact subassembly 50 is removably coupled to the electrode subassembly. In this way, the electrode subassembly 20 can be reused. Optionally, the electrically conductive polymer layer 40 of the electrode subassembly 20 can be cleaned prior to positioning the new skin contact subassembly 50 against the electrically conductive polymer layer 40 of the electrode subassembly 20.

In aspects in which the skin contact subassembly 50 (or electrode subassembly 20) comprises at least one alignment feature that provides an indication of a desired position of the electrode subassembly 20 relative to the skin contact subassembly 50, the at least one alignment feature can be used to orient the electrode subassembly 20 relative to the skin contact subassembly 50. Alignment features are discussed further below with respect to FIGS. 11-13.

A first kit can comprise an electrode subassembly 20 comprising at least one electrode element 30 having a skin-facing side 32 and a skin-facing surface 34. An electrically conductive polymer layer 40 can be positioned on the skin-facing side 32 of the at least one electrode element 30. The electrically conductive polymer layer 40 can have a skin-facing surface 42 which defines a skin-facing surface 22 of the electrode subassembly 20. Optionally, the electrode subassembly 20 can comprise the three-layer unit comprising the layer of anisotropic conductive material 70, as described herein. The kit can further comprise a plurality of skin contact subassemblies 50. Each skin contact subassembly 50 can comprise a skin contact conductive adhesive or gel 52. The skin contact conductive adhesive or gel 52 of each skin contact subassembly 50 can be configured to contact skin 300 of a subject. Any exposed adhesive or gel surface may be protected in the kit by covering the adhesive/gel surface with a release liner. For example, in some embodiments, one or both sides of the skin contact subassembly 50 may be provided with a release liner, each of which may be removed when the adhesive/gel surface is ready for use (for example, when the two subassemblies are to be combined, or the skin contact conductive adhesive or gel 52 is to be adhered to the subject's skin). When the skin contact subassembly 50 is disposed against the electrically conductive polymer layer 40 of the electrode subassembly 20, the skin contact conductive adhesive or gel 52 can be configured to electrically couple to the at least one electrode element 30 and the skin contact subassembly 50 can be configured to couple to the electrode subassembly as a removable unit.

In some aspects, the skin contact subassemblies 50 of the first kit can each comprise a three-layer unit comprising the skin contact conductive adhesive or gel 52, a layer of anisotropic conductive material 70, and a second conductive adhesive or gel layer 78. In some aspects, the three-layer unit can further comprise an edge sealing non-conductive border such as a strip of tape that covers the perimeter edge of the three layers and, optionally adheres to the top and bottom surface of the three layer unit. The layer of anisotropic conductive material 70 can have a skin facing side 72 with a skin facing surface 74 and an opposing outwardly facing surface 76. The skin facing surface 74 of the layer of anisotropic conductive material can be in contact with the skin contact conductive adhesive or gel 52 (optionally, hydrogel 53). The outwardly facing surface 76 of the layer of anisotropic conductive material 70 can be in contact with the second conductive adhesive or gel layer 78. In other respects, the components of the kit (e.g., the electrode subassembly 20 and the skin contact subassembly 50), the construction of the components, and the methods of use for the components of the kit can be as described above.

Figure 14:
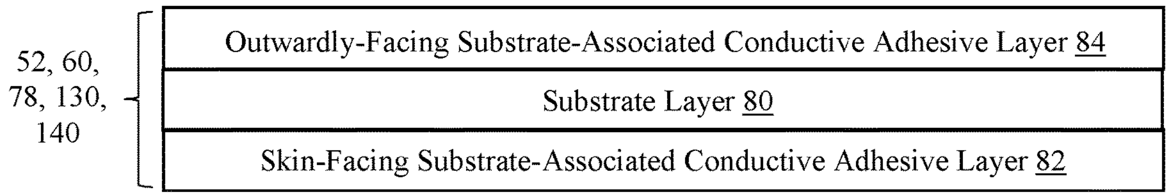
FIG. 14 is a schematic cross-sectional representation of an exemplary conductive adhesive structure comprising a substrate with opposed conductive adhesive or gel layers.

Referring to FIG. 14, in some aspects, one or more of the electrode subassembly conductive adhesive or gel 60, the skin contact conductive adhesive or gel 52 and the second conductive adhesive or gel 78 (for example, FIG. 2) can comprise a substrate layer 80, a skin-facing substrate-associated conductive adhesive or gel layer 82 and an outwardly-facing substrate-associated conductive adhesive or gel layer 84. In some aspects, the substrate layer 80 can have a continuous, uninterrupted structure, and the substrate layer can be electrically conductive. In other aspects, the substrate layer 80 can have an at least partially open structure that is configured to permit contact of adhesive layers 82, 84 from either side of the substrate layer. In exemplary aspects, the substrate 80 can comprise a mesh or a scrim.

In some aspects, the electrode subassembly can comprise the three-layer construct (a double layer of conductive adhesive or gel separated by a substrate layer, shown in FIG. 14) comprising the substrate layer 80, the skin-facing substrate-associated conductive adhesive or gel layer 82 and the outwardly-facing substrate-associated conductive adhesive or gel layer 84. In some aspects, the skin contact subassembly can comprise the three-layer construct (a double layer of conductive adhesive or gel separated by a substrate layer, shown in FIG. 14) comprising the substrate layer 80, the skin-facing substrate-associated conductive adhesive or gel layer 82 and the outwardly-facing substrate-associated conductive adhesive or gel layer 84.

In some aspects, a double layer of conductive adhesive or gel separated by a substrate layer (for example, the three-layer construct comprising the substrate layer 80, the skin-facing substrate-associated conductive adhesive or gel layer 82 and the outwardly-facing substrate-associated conductive adhesive or gel layer 84, shown in FIG. 14) can function as the skin contact subassembly that can be removably coupled to the electrode subassembly. This same construct can also be used as the skin contact subassembly in kits described herein, wherein, optionally, the exposed adhesive/gel surface(s) may be protected by release liner(s). In each of these embodiments, either the skin-facing substrate-associated conductive adhesive or gel layer 82 or the outwardly-facing substrate-associated conductive adhesive or gel layer 84, or both, may be a conductive adhesive, such as a conductive adhesive composite (described herein). Further, in each of these embodiments, either the skin-facing substrate-associated conductive adhesive or gel layer 82 or the outwardly-facing substrate-associated conductive adhesive or gel layer 84, or both, may be a hydrogel.

In various aspects, one or more of the electrode subassembly conductive adhesive or gel 60, the skin contact conductive adhesive or gel 52, the second conductive adhesive or gel 78, the skin-facing substrate-associated conductive adhesive or gel layer 82 or the outwardly-facing substrate-associated conductive adhesive or gel layer 84 can be hydrogel. In various aspects, one or more of the electrode subassembly conductive adhesive or gel 60, the skin contact conductive adhesive or gel 52, the second conductive adhesive or gel 78, the skin-facing substrate-associated conductive adhesive or gel layer 82 or the outwardly-facing substrate-associated conductive adhesive or gel layer 84 can be a conductive adhesive composite. The conductive adhesive composite can comprise a dielectric material and conductive particles dispersed therethrough. For example, the conductive particles can comprise carbon. In exemplary aspects, the conductive particles can comprise one or more of: graphite powder, carbon flakes, carbon fibers, carbon granules, carbon nanotubes, carbon nanowires, carbon black powder, or carbon microcoils. In some aspects, the conductive particles can comprise metal. The dielectric material may be, for example, an acrylic polymer (e.g., an acrylic adhesive). In some aspects, the dielectric material may be, for example, a silicone polymer (e.g., a silicone adhesive).

In exemplary aspects, the electrode subassembly conductive adhesive or gel 60 and conductive polymer layer 40 can cooperate to have a thickness from about 40 μm to about 2000 μm, such as from about 300 μm to about 700 μm. In exemplary aspects, the skin contact subassembly 50 can have a thickness from about 100 μm to about 400 μm, such as, for example, 200-250 μm.

Figure 15:
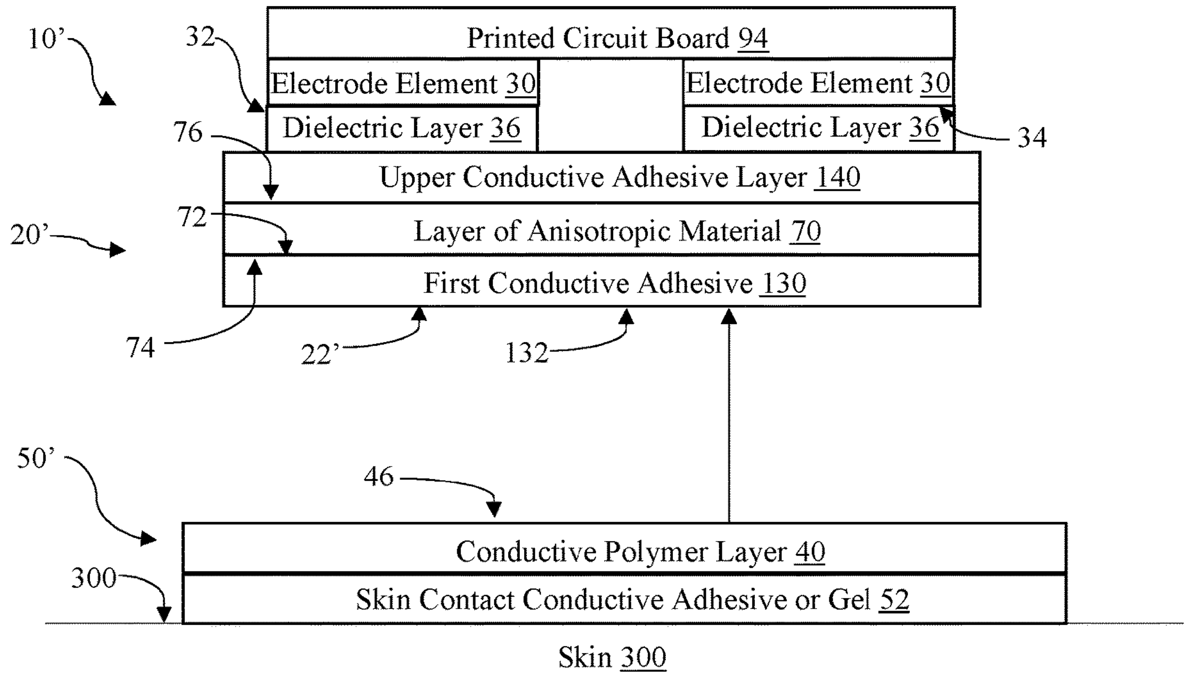
FIGS. 15-17 are schematic cross-sectional representations of exemplary treatment assemblies as disclosed herein, taken in the plane 2-2' of FIG. 1, according to various non-limiting embodiments.

Referring to FIG. 15, in another embodiment, an apparatus 10' can comprise an electrode subassembly 20' comprising at least one electrode element 30 having a skin-facing side 32 and a skin-facing surface 34. The electrode subassembly 20' can further comprise a first conductive adhesive or gel 130 on the skin-facing side of the at least one electrode element 30. The first conductive adhesive or gel 130 can have a skin-facing surface 132 which defines a skin-facing surface 22' of the electrode subassembly 20'. The apparatus 10' can further comprise a skin contact subassembly 50' removably coupled to the electrode subassembly 20'. The skin contact subassembly 50' can comprise an electrically conductive polymer layer 40 configured to removably couple to the skin-facing surface 22' of the electrode subassembly 20'. The skin contact subassembly 50' can further comprise a skin contact conductive adhesive or gel 52 configured to contact skin 300 of a subject. The skin contact conductive adhesive or gel 52 can be electrically coupled to the at least one electrode element 30 when the conductive polymer layer 40 of the skin contact subassembly 50' is disposed against the skin-facing surface 22' of the electrode subassembly 20'.

In some aspects, the electrically conductive polymer layer 40 of the skin contact subassembly 50' can be a non-adhesive electrically conductive polymer layer. In some aspects, the electrically conductive polymer layer 40 of the skin contact subassembly 50' can comprise a rubber or elastomer. In some aspects, the electrically conductive polymer layer 40 of the skin contact subassembly 50' can comprise an adhesive or sealant. In some aspects, the electrically conductive polymer layer 40 of the skin contact subassembly 50' can comprise a silicone polymer. In some aspects, the electrically conductive polymer layer of the skin contact subassembly can comprise a polydimethylsiloxane (PDMS). In some aspects, the electrically conductive polymer layer 40 of the skin contact subassembly 50' can comprise, for example, and without limitation, one or more of silicone rubber, silicone elastomer, natural rubber, poly cis-isoprene, polyisobutylene, polychloroprene, cis-polybutadiene, styrene-butadiene polymer, styrene-acrylonitrile-butadiene polymer, polyurethane, EPDM polymer, AEM polymer, EVA polymer, fluoropolymer, and perfluoropolymer. In some aspects, the electrically conductive polymer layer 40 of the skin contact subassembly 50' can comprise polyetherimide, polyetherketone, polyethersulfone, polyether ether ketone, or polyaryl ether ketone.

In some aspects, the electrically conductive polymer layer 40 of the skin contact subassembly 50' can comprise a composite material having conductive particles dispersed therethrough. For example, the conductive particles can comprise carbon. In exemplary aspects, the conductive particles can comprise one or more of: graphite powder, carbon flakes, carbon fibers, carbon granules, carbon nanotubes, carbon nanowires, carbon black powder, or carbon microcoils. In some aspects, the conductive particles can comprise metal.

In some aspects, the electrode subassembly 20' can further comprise a dielectric layer 36 between the at least one electrode element 30 and the electrically conductive polymer layer 40 of the skin contact subassembly 50'. The dielectric layer 36 of the electrode subassembly 20' can be positioned between the at least one electrode element 30 and the first conductive adhesive 130. For example, the dielectric layer 36 of the electrode subassembly 20' can be positioned between the at least one electrode element 30 and the upper conductive adhesive layer 140.

In some aspects, the dielectric layer 36 can comprise a ceramic or a dielectric polymer. In aspects in which the dielectric layer 36 comprises a dielectric polymer, the dielectric polymer has a dielectric constant greater than 10 or greater than 20. In some aspects, the electrode subassembly 20' does not include a dielectric layer 36.

In some aspects, the apparatus 10' does not comprise an additional adhesive (such as a structural adhesive) between the skin contact subassembly 50' and the first conductive adhesive or gel 130 of the electrode subassembly 20'. The first conductive adhesive or gel 130 of the electrode subassembly 20' and the skin contact subassembly 50' can be removably coupled by a physical, non-chemical adhesion. For example, the first conductive adhesive or gel 130 of the electrode subassembly 20' and the skin contact subassembly 50' can be removably coupled by a Van der Waals attractive force (e.g., a weak Van der Waals attractive force). In some aspects, the weak Van der Waals attractive force may be supplemented, as discussed further herein.

In some aspects, the outwardly facing surface 46 of the electrically conductive polymer layer 40 of the skin contact subassembly 50' can be smooth.

In exemplary aspects, the electrically conductive polymer layer 40 of the skin contact subassembly 50' is not tacky.

In some aspects, the skin contact subassembly 50' can comprise acrylic adhesive. For example, the skin contact conductive adhesive or gel 52 can comprise an acrylic adhesive.

In some aspects, the electrode subassembly 20' can further comprise a layer of anisotropic conductive material 70 having a skin-facing side 72 with a skin-facing surface 74 and an opposing outwardly facing surface 76. The layer of anisotropic conductive material 70 can be disposed in contact with the first conductive adhesive or gel 130.

In some optional aspects, the electrode subassembly 20' can comprise a three layer unit comprising the first conductive adhesive or gel 130, a layer of anisotropic conductive material 70, and an upper conductive adhesive or gel 140. The layer of anisotropic conductive material 70 can have a skin facing side 72 with a skin facing surface 74 and an opposing outwardly facing surface 76. The skin facing surface 74 of the layer of anisotropic conductive material 70 can be in contact with the first conductive adhesive or gel 130, and the outwardly facing surface 76 of the layer of anisotropic conductive material 70 can be in contact with the upper conductive adhesive or gel 140.

Figure 16:
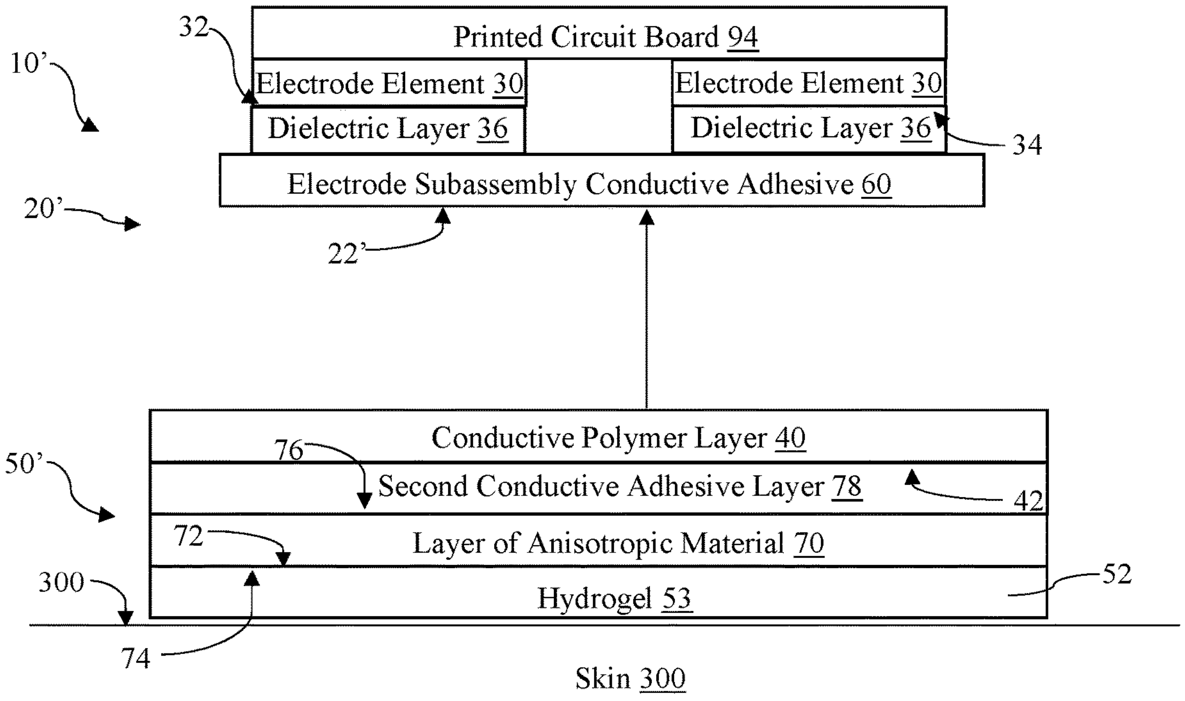

In other aspects, and referring to FIG. 16, the electrode subassembly 20' does not include the layer of anisotropic conductive material 70. In such cases, the skin facing surface 22' of the electrode subassembly 20' can be provided by an electrode subassembly conductive adhesive 60. In other respects, the electrode subassembly 20' of FIG. 16 may be similar to that described for the electrode subassembly 20' of FIG. 15.

Figure 17:
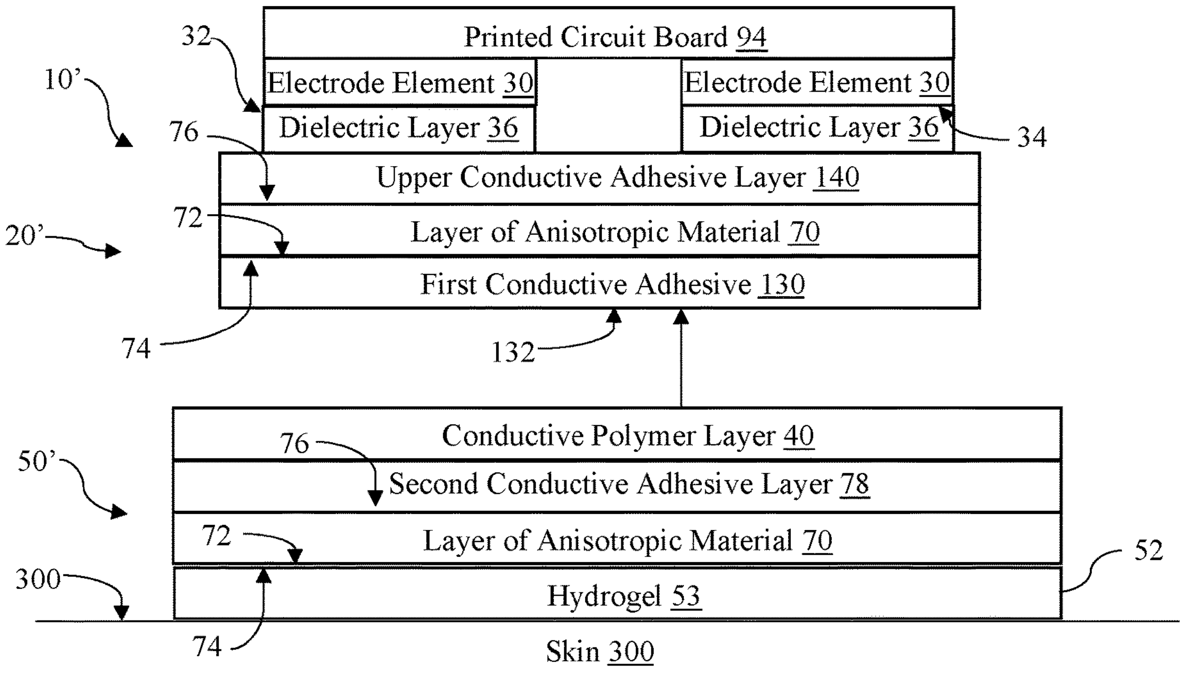

Referring to FIGS. 16-17 (and following the labelling scheme above), in some aspects, the skin contact subassembly 50' can comprise a layer of anisotropic conductive material 70. For example, the skin contact subassembly 50' can comprise a second conductive adhesive layer 78 between the layer of anisotropic conductive material 70 and the electrically conductive polymer layer 40. The skin contact subassembly 50' can further comprise the skin contact conductive adhesive or gel 52 on the skin side of the layer of anisotropic conductive material 70 opposite the second conductive adhesive layer 78. Optionally, the skin contact conductive adhesive or gel 52 can comprise hydrogel 53 (see, for example, FIGS. 16-17). In further aspects, the skin contact subassembly 50' can further comprise a skin-side conductive adhesive or gel between the layer of anisotropic conductive material 70 and the skin contact conductive adhesive or gel 52 (e.g., optionally, hydrogel 53). For example, the additional skin-side conductive adhesive or gel may be a conductive adhesive composite and the skin contact conductive adhesive or gel may be a hydrogel. In other aspects, as illustrated in FIGS. 16-17, the skin-side conductive adhesive or gel can be omitted.

In some aspects, and as illustrated in FIG. 17, each of the electrode subassembly 20' and the skin contact subassembly 50' can comprise a layer of anisotropic conductive material 70. In other aspects, and with reference to FIG. 16, the layer of anisotropic conductive material 70 can be provided only in the skin contact subassembly 50. In other respects, the constructs shown in FIGS. 16-17 may be similar to those described for the FIG. 15 embodiment (and following the same labelling scheme).

A method of using the apparatus 10' can comprise removing the skin contact subassembly 50' from the first conductive adhesive or gel 130 (FIGS. 15 and 17) of the electrode subassembly 20' or from the electrode subassembly conductive adhesive 60 (FIG. 16) of the electrode subassembly 20'. A new skin contact subassembly 50' can be positioned against the first conductive adhesive or gel 130 of the electrode subassembly 20' (FIGS. 15 and 17) or against the electrode subassembly conductive adhesive 60 (FIG. 16) so that the new skin contact subassembly 50' is removably coupled to the electrode subassembly 20'. The first conductive adhesive or gel 130 (or the electrode subassembly conductive adhesive 60) of the electrode subassembly 20' can be cleaned prior to positioning the new skin contact subassembly 50' against the first conductive adhesive or gel 130 (or the electrode subassembly conductive adhesive 60) of the electrode subassembly 20'.

In aspects in which the skin contact subassembly 50' (or electrode subassembly 20') comprises at least one alignment feature that provides an indication of a desired position of the electrode subassembly relative to the skin contact subassembly, the at least one alignment feature can be used to orient the electrode subassembly relative to the skin contact subassembly (as discussed below with respect to FIGS. 11-13).

A second kit can comprise an electrode subassembly 20' comprising at least one electrode element 30 having a skin-facing side 32 and a skin-facing surface 34. The electrode subassembly 20' can further comprise a first conductive adhesive or gel 130 (FIGS. 15 and 17) or an electrode subassembly conductive adhesive 60 (FIG. 16) on the skin-facing side of the at least one electrode element 30. The first conductive adhesive or gel 130' can have a skin-facing surface (for example, surface 132 in FIGS. 15 and 17, or surface 22' in FIG. 16) that defines a skin-facing surface 22' of the electrode subassembly 20'.

The second kit can further comprise a plurality of skin contact subassemblies 50', each skin contact subassembly comprising: an electrically conductive polymer layer 40 configured to be disposed on the skin-facing surface 22' of the electrode subassembly 20' and a skin contact conductive adhesive or gel 52 (optionally, hydrogel 53). The skin contact conductive adhesive or gel 52 of each skin contact subassembly 50' of the plurality of skin contact subassemblies can be configured to contact skin 300 of a subject. Optionally, the skin contact subassembly 50' can include the three-layer unit comprising the layer of anisotropic conductive material 70 as described herein. As discussed above, any exposed adhesive or gel surface may be protected in the kit by covering the adhesive/gel surface with a release liner. The release liner(s) may be removed when the adhesive/gel surface is ready for use (for example, when the two subassemblies are to be combined, or the skin contact conductive adhesive or gel is to be adhered to the subject's skin). When the skin contact subassembly 50' is disposed against the skin-facing surface 22' of the electrode subassembly 20', the skin contact conductive adhesive or gel 52 can be configured to electrically couple to the at least one electrode element 30 and the skin contact subassembly 50' is configured to couple to the electrode subassembly 20' as a removable unit.

In some aspects, the electrode subassembly 20' can comprise a three-layer unit comprising the first conductive adhesive or gel 130, a layer of anisotropic conductive material 70, and an upper conductive adhesive or gel 140. The layer of anisotropic conductive material 70 can have a skin facing side 72 with a skin facing surface 74 and an opposing outwardly facing surface 76. The skin facing surface 74 of the layer of anisotropic conductive material 70 can be in contact with the first conductive adhesive or gel 130, and the outwardly facing surface 76 of the layer of anisotropic conductive material can be in contact with the upper conductive adhesive or gel 140. In other respects, the components of the kit (e.g., the electrode subassembly and the skin contact subassembly), the construction of the components, and the methods of use for the components of the kit can be as described above.

Exemplary Aspects of the Disclosed Apparatuses, Kits, and Methods

As previously described for the embodiments of FIG. 2, any of the conductive adhesive or gel components of embodiments of FIGS. 2-10, or FIGS. 15-17, may also be present as the three-layer structure of FIG. 14 and constructed similarly to that described above with respect to FIG. 14. That is, any layer of conductive adhesive or gel described herein (including adhesive layers 52, 60, 78, 130 and 140) may take the form of a double layer of conductive adhesive or gel separated by a substrate layer as described above, wherein the double layer of conductive adhesive or gel may be the same conductive adhesive or gel or a different conductive adhesive or gel either side of the substrate. For example, referring to FIGS. 14 and 15, in some aspects, one or more of the skin contact conductive adhesive or gel 52, the first conductive adhesive or gel 130, or the upper conductive adhesive or gel 140 can comprise a substrate layer 80, a skin-facing substrate-associated conductive adhesive or gel layer 82 and an outwardly-facing substrate-associated conductive adhesive or gel layer 84. In some aspects, the substrate layer 80 can have a continuous, uninterrupted structure, and the substrate layer can be electrically conductive. In other aspects, the substrate layer 80 can have an at least partially open structure that is configured to permit contact of adhesive layers 82, 84 from either side of the substrate layer. In exemplary aspects, the substrate 80 can comprise a mesh or a scrim.

In various aspects, including the embodiments of FIGS. 2-10 and 14-17, one or more of the electrode subassembly conductive adhesive or gel 60, the second conductive adhesive or gel 78, the skin contact conductive adhesive or gel 52, the skin-facing substrate-associated conductive adhesive or gel layer 82 or the outwardly-facing substrate-associated conductive adhesive or gel layer 84 can be a hydrogel. Similarly, the first conductive adhesive or gel 130 and/or the upper conductive adhesive or gel layer 140 can be a hydrogel. In various aspects, including the embodiments of FIGS. 2-10 and 14-17, one or more of the electrode subassembly conductive adhesive or gel 60, the second conductive adhesive or gel 78, the skin contact conductive adhesive or gel 52, the skin-facing substrate-associated conductive adhesive or gel layer 82 or the outwardly-facing substrate-associated conductive adhesive or gel layer 84 can be a conductive adhesive composite. Similarly, the first conductive adhesive or gel 130 and/or the upper conductive adhesive or gel layer 140 can be a conductive adhesive composite. The conductive adhesive composite can comprise a dielectric material and conductive particles dispersed therethrough. For example, the conductive particles can comprise carbon. In exemplary aspects, the conductive particles can comprise one or more of: graphite powder, carbon flakes, carbon fibers, carbon granules, carbon nanotubes, carbon nanowires, carbon black powder, or carbon microcoils. In some aspects, the conductive particles can comprise metal. The dielectric material may be, for example, an acrylic polymer (e.g., an acrylic adhesive). In some aspects, the dielectric material may be, for example, a silicone polymer (e.g., a silicone adhesive).

In various aspects, and as further described herein, the conductive adhesives disclosed herein can comprise a conductive adhesive composite, a hydrogel, or other suitable conductive material. For example, in some aspects, one or more of the conductive adhesives 52, 60, 78, 82, 84, 130, 140 can comprise hydrogel.

Further, as discussed above, it is contemplated that one or more of the conductive adhesive layers 52, 60, 78, 82, 84, 130, 140 disclosed herein can comprise conductive adhesive composites (described further below) rather than hydrogel. In exemplary aspects, the conductive adhesive composite can comprise a dielectric material and conductive particles dispersed within the dielectric material. In some embodiments, at least a portion of the conductive particles can define a conductive pathway through a thickness of the conductive adhesive composite. In some embodiments, it is contemplated that the conductive particles can be aligned in response to application of an electric field such that the conductive particles undergo electrophoresis. In some aspects, the dielectric material of the conductive adhesive composites is a polymeric adhesive. Optionally, in these aspects, the polymeric adhesive can be an acrylic adhesive. In some aspects, the conductive particles can comprise carbon. Optionally, in these aspects, the conductive particles can comprise graphite powder. Additionally, or alternatively, the conductive particles can comprise carbon flakes. Additionally, or alternatively, the conductive particles can comprise carbon granules. Additionally, or alternatively, the conductive particles can comprise carbon nanotubes. Additionally, or alternatively, the conductive particles can comprise carbon black powder. Additionally, or alternatively, the conductive particles can comprise carbon microcoils. In further aspects, the conductive adhesive composite further comprises a polar material (e.g., a polar salt). The polar salt can be a quaternary ammonium salt, such as a tetra alkyl ammonium salt. Exemplary conductive adhesive composites, as well as methods for making such conductive adhesive composites, are disclosed in U.S. Pat. Nos. 8,673,184 and 9,947,432, which are incorporated herein by reference for all purposes. In exemplary aspects, the conductive adhesive composite can be a dry carbon/salt adhesive, such as the OMNI-WAVE™ adhesive compositions manufactured and sold by FLEXCON® (Spencer, MA, USA); or ARcare® 8006 electrically conductive adhesive composition manufactured and sold by Adhesives Research, Inc. (Glen Rock, PA, USA). In further exemplary aspects, it is contemplated that the conductive adhesive composite can comprise a layer of an electrically conductive adhesive, such as for example, from use (by removal of the transfer film layer) of Electrically Conductive Adhesive Transfer Tape 9712 or Electrically Conductive Adhesive Transfer Tape 9713 (both manufactured by 3M™, St. Paul, MN, USA). As an example, the 3-layer skin contact subassembly 50 illustrated in FIG. 2 could comprise a layer of anisotropic material 70 (as described above, such as, for example, a sheet of pyrolytic graphite) sandwiched between two layers of conductive adhesive composite, which may or may not be the same. For example, one layer of conductive adhesive composite may comprise an acrylic adhesive, and the other layer of conductive adhesive composite may comprise a silicone adhesive; or both layers may comprise an acrylic adhesive; or both layers may comprise a silicone adhesive. For example, the skin contact conductive adhesive or gel 52 could be an acrylic adhesive filled with carbon fibers, and the second conductive adhesive layer 78 could be an acrylic adhesive filled with carbon powder; or vice-versa; or both acrylic adhesives could utilize the same type of filler particles. In each case, the two acrylic adhesives may be the same or may be different. Alternatively, in some aspects, the skin contact conductive adhesive or gel 52 could be a silicone adhesive filled with carbon fibers, and the second conductive adhesive layer 78 could be a silicone adhesive filled with carbon powder; or vice-versa; or both silicone adhesives could utilize the same type of filler particles. In each case, the two silicone adhesives may be the same or may be different. Further, in some aspects, one adhesive layer may be an acrylic adhesive, and the other may be a silicone adhesive (and vice-versa); and each adhesive (individually) can have conductive particles (for example, either carbon fibers or carbon powder as a conductive filler), which may be the same or may be different in the two adhesives. One can further envision other options using other adhesive compositions and other conductive particle fillers. The same options for conductive adhesive layers exist for other embodiments using the 3-layer unit comprising a layer of anisotropic material 70 sandwiched between two layers of conductive adhesive whether in the skin contact subassembly 50, 50' or in the electrode subassembly 20, 20'.

In some aspects, either the electrode subassembly (20, 20'), or the skin contact subassembly (50, 50'), or both, may comprise a layer of anisotropic conductive material 70. In some aspects, the layer of anisotropic conductive material 70 can be or can comprise a synthetic graphite. In additional aspects, the layer of anisotropic conductive material 70 can be or can comprise a layer of pyrolytic graphite, graphitized polymer film, or graphite foil made from compressed high purity exfoliated mineral graphite. In other aspects, other anisotropic materials may be suitable as the layer of anisotropic conductive material 70.

The layer of anisotropic conductive material 70 can have a first thermal conductivity in a direction that is perpendicular to the skin facing surface. In some optional aspects, thermal conductivity of the sheet in directions that are parallel to the skin facing surface can be more than two times higher than the first thermal conductivity For example, the thermal conductivity of the sheet in directions that are parallel to the skin facing surface may be more than: 1.5 times, 2 times, 3 times, 5 times, 10 times, 20 times, 30 times, 100 times, 200 times, or even more than 1,000 times higher than the first thermal conductivity. In some embodiments, the thermal conductivity of the sheet of anisotropic material in directions that are parallel to the skin facing surface is between 1.5 times and 1000 times higher, such as between 5 times and 30 times higher, than the first thermal conductivity. The layer of anisotropic conductive material 70 can further have a first resistance in a direction that is perpendicular to the skin facing surface. In some optional aspects, resistance of the sheet in directions that are parallel to the skin facing surface can be less than half of the first resistance. For example, the resistance of the sheet 70 in directions that are parallel to the skin facing surface may be less than: 75%, 50%, 40%, 30%, 20%, 10%, 5%, 1%, 0.5%, 0.1%, or even less than 0.05% of the first resistance. In some embodiments, the resistance of the sheet of anisotropic material in directions that are parallel to the skin facing surface is between 0.05% and 75% of the first resistance, such as between 0.05% and 10% of the first resistance. In some aspects, either the electrode subassembly (20, 20'), or the skin contact subassembly (50, 50'), or both, do not include a layer of anisotropic conductive material 70.

The electrode subassembly 20 or 20' can have an operative conductive area. For example, as shown in FIG. 1, in aspects in which the electrode subassembly 20 (or 20') does not comprise a layer of anisotropic conductive material 70, the operative conductive area 90 can be defined by an outer perimeter that surrounds every electrode of the at least one electrode (e.g., an areal footprint of the at least one electrode element). In aspects in which the electrode subassembly 20 (or 20') comprises a layer of anisotropic conductive material 70, the operative conductive area 90' can be defined by the outer perimeter of the anisotropic material. In some aspects, the skin contact subassembly 50 can overlie an entirety of the operative conductive area (90 or 90'). In further aspects, the skin contact subassembly 50 can extend past the operative conductive area (90 or 90'). For example, the skin contact subassembly 50 can extend past the operative conductive area (90 or 90') by at least 1 mm, or at least 2 mm, or at least 5 mm, or at least 10 mm or more. In further aspects, the skin contact subassembly 50 can fit within the operative conductive area (90 or 90').

Figure 11:
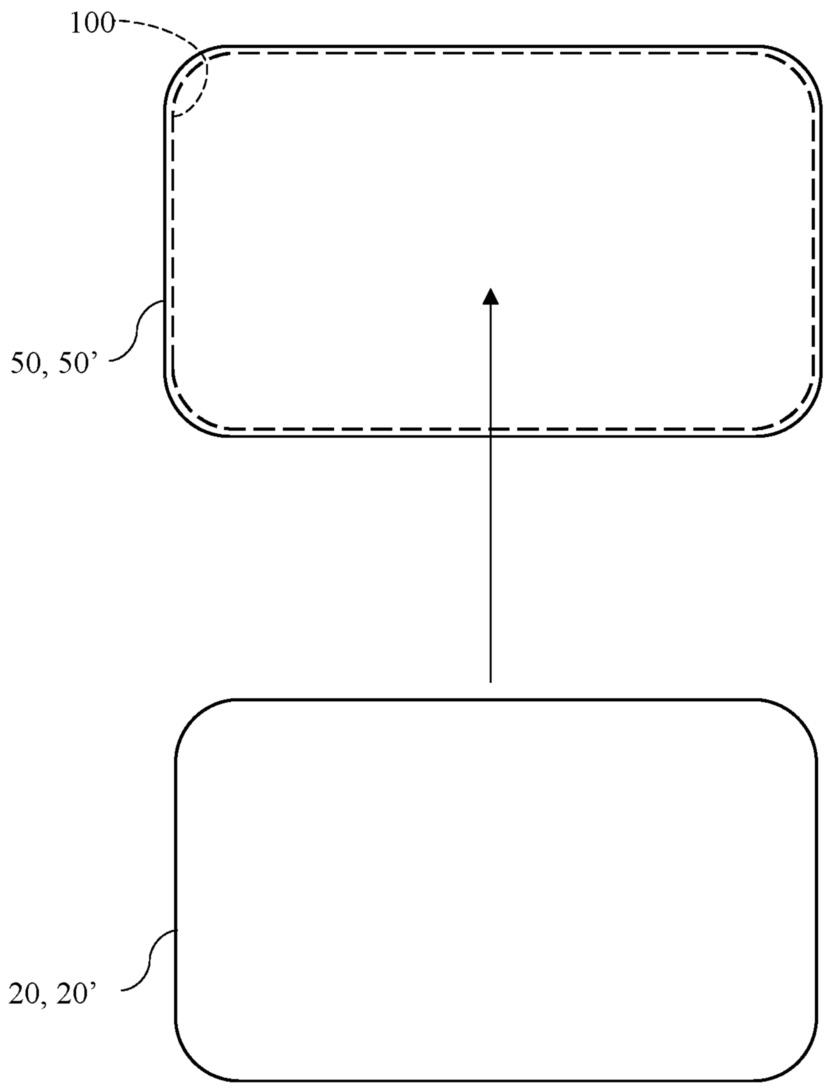
FIGS. 11-13 are schematic representations of exemplary systems for aligning an electrode subassembly and a skin contact subassembly of the treatment assembly of FIG. 1, according to various non-limiting embodiments.
Figure 12:
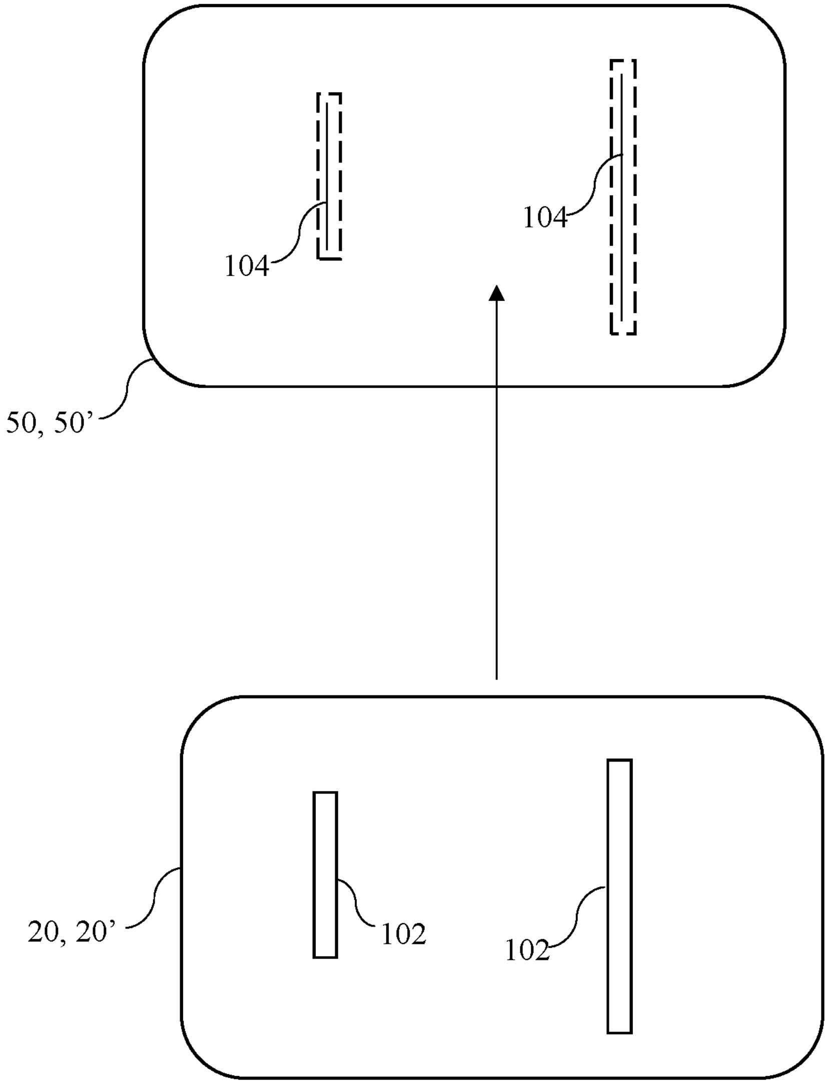
Figure 13:
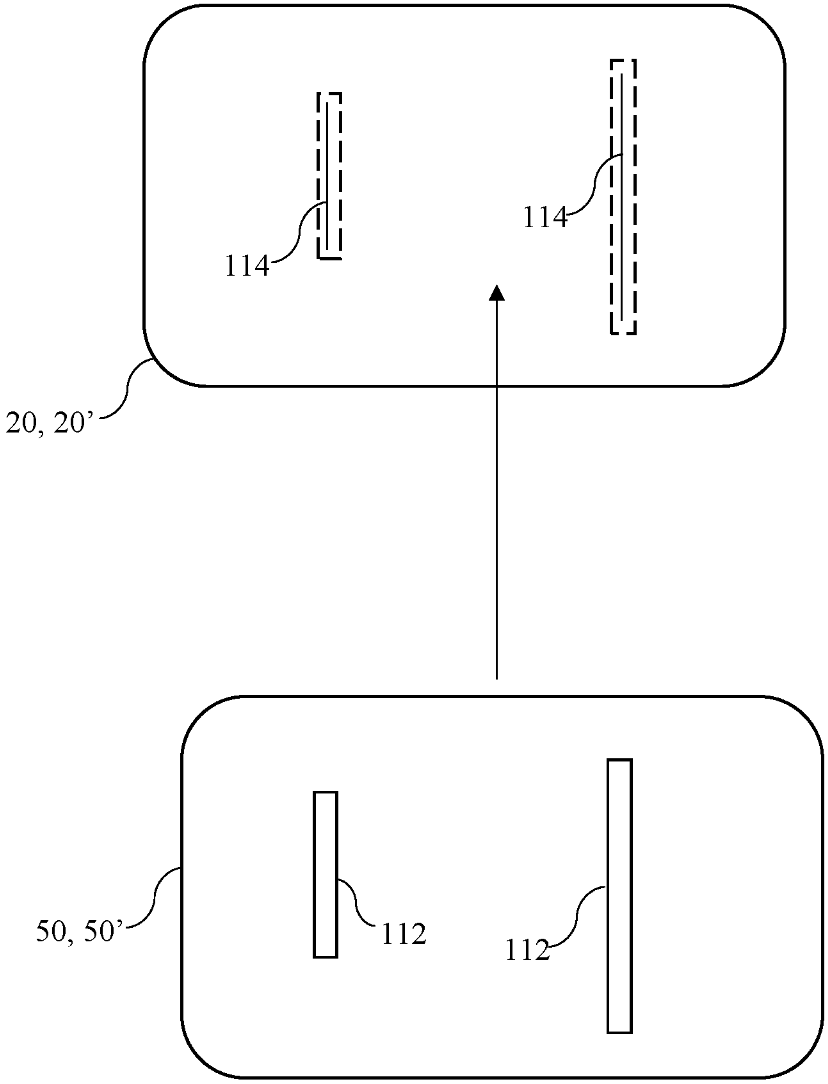

Referring to FIGS. 11-13, the skin contact subassembly 50, 50' can comprise at least one alignment feature 100 that provides an indication of a desired position of the electrode subassembly 20, 20' relative to the skin contact subassembly 50, 50', in which the electrode subassembly 20, 20' is positioned within the outer periphery of the skin contact subassembly 50, 50' (and, conversely, the skin contact subassembly 50, 50' overlies an entirety of the operative conductive area 90 or 90' (shown in FIG. 1). For example, referring to FIG. 11, the alignment feature 100 on the skin contact subassembly 50, 50' can comprise an outline of at least a portion of a perimeter of the electrode subassembly 20, 20'. In other aspects, and with reference to FIG. 12, the electrode subassembly 20, 20' can define at least one opening 102 therethrough. The alignment feature 100 can be an opening 102 and the skin contact subassembly 50, 50' can comprise a corresponding marking 104 on the skin contact subassembly 50, 50' that is viewable through each opening 102 of the at least one opening through the electrode subassembly 20, 20' when the electrode subassembly is in the desired position relative to the skin contact subassembly.

In still further aspects, the skin contact subassembly 50, 50' can have a greater footprint than the electrode subassembly 20, 20' so that an entirety of the electrode subassembly overlies the skin contact subassembly within the footprint of the skin contact subassembly (e.g., so that some or all of the outer perimeter of the skin contact subassembly extends outwardly beyond the outer perimeter of the electrode subassembly). It is contemplated that such an arrangement can permit easier attachment and separation of the skin contact subassembly 50, 50' and the electrode subassembly 20, 20', permitting an outer periphery of the skin contact subassembly to be seen around the edges of the electrode subassembly. For embodiments including a layer of anisotropic conductive material in the skin contact subassembly, a larger areal footprint for the skin contact subassembly also allows for spreading of the heat and current laterally over a greater are of the skin, thereby helping to avoid the formation of any hotspots beneath the electrodes. However, in other aspects, the electrode subassembly 20, 20' can have a greater footprint than the skin contact subassembly 50, 50' so that an entirety of the skin contact subassembly is within the footprint of the electrode subassembly. In still other aspects, the electrode subassembly 20, 20' and the skin contact subassembly 50, 50' can have the same, or substantially the same footprint.

In some aspects, and with reference to FIG. 13, the skin contact subassembly 50, 50' can define at least one opening 112 therethrough. The alignment feature 100 can comprise the at least one opening. The electrode subassembly 20, 20' can comprise a corresponding marking 114 that is viewable through each opening 112 of the at least one opening through the skin contact subassembly 50, 50' when the skin contact subassembly is in the desired position relative to the electrode subassembly 20, 20'.

In some optional aspects, the apparatus 10, 10' can comprise a plurality of electrode elements 30. In these aspects, the electrode elements 30 can be wired together (e.g., using wires, or traces on a printed circuit board 94 that can optionally be a flex circuit, etc.). Optionally, a cover tape or bandage on the electrode subassembly may be used to hold the electrodes in place. In other aspects, the apparatus 10, 10' can have only one single electrode element. That is, the apparatus 10, 10' has exactly one electrode).

In some aspects, and optionally, the periphery of either the electrode subassembly 20, 20', or the skin contact subassembly 50, 50', or both, may additionally include an affixed reversible fastener, such as, for example, a hook and loop fastener material; a snap fastener, such as, for example, a fastener material based on flexible projection bodies and widened (e.g., mushroom-shaped) heads designed to interlock with similar opposingly faced fastener material of similarly-shaped (e.g., mushroom-shaped) heads; or magnets, any of which can help to support the adjoining of the electrode subassembly 20, 20' with the skin contact subassembly 50, 50'. An example of hook and loop material is Velcro™ fastener (Velcro USA, Inc., Manchester, NH, USA), and an example of fasteners based on interlocking mushroom heads is DUAL-LOCK™ reclosable fastener (3M™, St. Paul, MN, USA). Alternatively, the periphery of either the electrode subassembly 20, 20', or the skin contact subassembly 50, 50', or both, may additionally include an adhesive or adhesive tape; or one or more buttons and associated buttonholes; or a zipper mechanism.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising:

- an electrode subassembly comprising:
  - at least one electrode element having a skin-facing side and a skin-facing surface; and
  - an electrically conductive polymer layer on the skin-facing side of the at least one electrode element, wherein the electrically conductive polymer layer has a skin-facing surface which defines a skin-facing surface of the electrode subassembly; and
- a skin contact subassembly removably coupled to the electrode subassembly, wherein the skin contact subassembly comprises a skin contact conductive adhesive or gel configured to contact skin of a subject, wherein the skin contact conductive adhesive or gel is electrically coupled to the at least one electrode element when the skin contact subassembly is disposed against the skin-facing surface of the electrically conductive polymer layer of the electrode subassembly.

Aspect 2: The apparatus of aspect 1, wherein the electrically conductive polymer layer of the electrode subassembly comprises a rubber or elastomer.

Aspect 3: The apparatus of aspect 1, wherein the electrically conductive polymer layer of the electrode subassembly comprises an adhesive or sealant.

Aspect 4: The apparatus of any one of the preceding aspects, wherein the electrically conductive polymer layer of the electrode subassembly comprises a silicone polymer.

Aspect 5: The apparatus of aspect 1, wherein the electrically conductive polymer layer of the electrode subassembly is or comprises silicone rubber, silicone elastomer, natural rubber, poly cis-isoprene, polyisobutylene, polychloroprene, cis-polybutadiene, styrene-butadiene, styrene-acrylonitrile-butadiene, polyurethane, EPDM, EVA polymer, AEM polymer, fluoropolymer, or perfluoropolymer, or combinations thereof.

Aspect 6: The apparatus of any one of the preceding aspects, wherein the electrically conductive polymer layer of the electrode subassembly comprises a composite material having conductive particles dispersed therethrough.

Aspect 7: The apparatus of aspect 6, wherein the conductive particles comprise carbon.

Aspect 8: The apparatus of aspect 7 wherein the conductive particles comprise one or more of: graphite powder, carbon flakes, carbon fibers, carbon granules, carbon nanotubes, carbon nanowires, carbon black powder, or carbon microcoils.

Aspect 9: The apparatus of aspect 6, wherein the conductive particles comprise metal.

Aspect 10: The apparatus of any one of the preceding aspects, wherein the electrically conductive polymer layer of the electrode subassembly has an outwardly facing surface that faces the at least one electrode element, the electrode subassembly further comprising an electrode subassembly conductive adhesive or gel layer disposed against the outwardly facing surface of the electrically conductive polymer layer.

Aspect 11: The apparatus of any one of the preceding aspects, wherein the electrode subassembly further comprises a dielectric layer between the at least one electrode element and the electrically conductive polymer layer of the electrode subassembly.

Aspect 12: The apparatus of any one of the preceding aspects, wherein the electrode subassembly further comprises a dielectric layer between the at least one electrode element and the electrode subassembly conductive adhesive or gel layer.

Aspect 13: The apparatus of aspect 11 or aspect 12, wherein the dielectric layer comprises a ceramic or dielectric polymer.

Aspect 14: The apparatus of aspect 13, wherein the dielectric layer comprises a dielectric polymer, and wherein the dielectric polymer has a dielectric constant greater than 10.

Aspect 15: The apparatus of any one of the preceding aspects, wherein the apparatus does not comprise an additional adhesive between the skin contact subassembly and the electrically conductive polymer layer of the electrode subassembly.

Aspect 16: The apparatus of any one of the preceding aspects, wherein the electrically conductive polymer layer of the electrode subassembly and the skin contact subassembly are removably coupled by a physical, non-chemical adhesion.

Aspect 17: The apparatus of any one of the preceding aspects, wherein the electrically conductive polymer layer of the electrode subassembly and the skin contact subassembly are removably coupled by a Van der Waals attractive force.

Aspect 18: The apparatus of any one of the preceding aspects, wherein the skin facing surface of the electrically conductive polymer layer of the electrode subassembly is smooth.

Aspect 19: The apparatus of any one of the preceding aspects, wherein the electrically conductive polymer layer of the electrode subassembly is not tacky.

Aspect 20: The apparatus of any one of the preceding aspects, wherein the skin contact subassembly further comprises a layer of anisotropic conductive material.

Aspect 21: The apparatus of any one of the preceding aspects, wherein the skin contact subassembly further comprises a layer of anisotropic conductive material having a skin-facing side with a skin-facing surface and an opposing outwardly facing surface, wherein the layer of anisotropic conductive material is disposed in contact with the skin contact conductive adhesive or gel, and wherein the at least one electrode element is in electrical contact with the outwardly facing surface of the layer of anisotropic conductive material when the electrode subassembly is in contact with the skin contact subassembly.

Aspect 22: The apparatus of any one of the preceding aspects, wherein the skin contact conductive adhesive or gel comprises a conductive adhesive composite.

Aspect 23: The apparatus of aspects 22, wherein the conductive adhesive composite comprises conductive particles dispersed therethrough.

Aspect 24: The apparatus of aspect 23, wherein the conductive particles comprise carbon.

Aspect 25: The apparatus of aspect 24 wherein the conductive particles comprise one or more of: graphite powder, carbon flakes, carbon fibers, carbon granules, carbon nanotubes, carbon nanowires, carbon black powder, or carbon microcoils.

Aspect 26: The apparatus of aspect 23, wherein the conductive particles comprise metal.

Aspect 27: The apparatus of any one of the preceding aspects, wherein the skin contact subassembly further comprises a layer of anisotropic conductive material.

Aspect 28: The apparatus of any one of the preceding aspects, wherein the skin contact subassembly comprises a three layer unit comprising the skin contact conductive adhesive or gel, a layer of anisotropic conductive material, and a second conductive adhesive or gel layer; wherein the layer of anisotropic conductive material has a skin facing side with a skin facing surface and an opposing outwardly facing surface; and wherein the skin facing surface of the layer of anisotropic conductive material is in contact with the skin contact conductive adhesive or gel, and the outwardly facing surface of the layer of anisotropic conductive material is in contact with the second conductive adhesive or gel layer.

Aspect 29: The apparatus of aspect 28, wherein one or both of the skin contact conductive adhesive or gel and the second conductive adhesive or gel layer comprise:

a substrate layer;

a skin-facing substrate-associated conductive adhesive or gel layer; and an outwardly-facing substrate-associated conductive adhesive or gel layer.

Aspect 30: The apparatus of aspect 29, wherein the substrate layer has a continuous, uninterrupted structure, and wherein the substrate layer is electrically conductive.

Aspect 31: The apparatus of aspect 29, wherein the substrate layer has an at least partially open structure that is configured to permit contact of adhesive layers from either side of the substrate layer.

Aspect 32: The apparatus of aspect 31, wherein the substrate comprises a mesh or a scrim.

Aspect 33: The apparatus of aspect 29, wherein one or more of the second conductive adhesive or gel, the skin-facing substrate-associated conductive adhesive or gel layer or the outwardly-facing substrate-associated conductive adhesive or gel layer is a conductive adhesive composite.

Aspect 34: The apparatus of aspect 33, wherein the conductive adhesive composite comprises conductive particles dispersed therethrough.

Aspect 35: The apparatus of aspect 34, wherein the conductive particles comprise carbon.

Aspect 36: The apparatus of aspect 35 wherein the conductive particles comprise one or more of: graphite powder, carbon flakes, carbon fibers, carbon granules, carbon nanotubes, carbon nanowires, carbon black powder, or carbon microcoils.

Aspect 37: The apparatus of aspect 34, wherein the conductive particles comprise metal.

Aspect 38: The apparatus of any one of the preceding aspects, wherein the skin contact subassembly comprises acrylic adhesive.

Aspect 39: The apparatus of aspect 20, 21, 27, or aspect 28, wherein the layer of anisotropic conductive material is or comprises a synthetic graphite.

Aspect 40: The apparatus of aspect 21 or aspect 28, wherein the layer of anisotropic conductive material is or comprises a layer of pyrolytic graphite, graphitized polymer film, or graphite foil made from compressed high purity exfoliated mineral graphite.

Aspect 41: The apparatus of aspect 21 or aspect 28, wherein the layer of anisotropic conductive material has a first thermal conductivity in a direction that is perpendicular to the skin facing surface, and wherein thermal conductivity of the sheet in directions that are parallel to the skin facing surface is more than two times higher than the first thermal conductivity.

Aspect 42: The apparatus of aspect 21 or aspect 28, wherein the layer of anisotropic conductive material has a first resistance in a direction that is perpendicular to the skin facing surface, and wherein resistance of the sheet in directions that are parallel to the skin facing surface is less than half of the first resistance.

Aspect 43: The apparatus of any one of the preceding aspects, wherein the electrode subassembly has an operative conductive area, and wherein the skin contact subassembly has an areal footprint that overlies an entirety of the operative conductive area.

Aspect 44: The apparatus of any one of the preceding aspects, wherein the electrode subassembly has an operative conductive area, wherein the skin contact subassembly has an areal footprint that overlies an entirety of the operative conductive area, and wherein the skin contact subassembly comprises at least one alignment feature that provides an indication of a desired position of the electrode subassembly relative to the skin contact subassembly.

Aspect 45: The apparatus of aspect 44, wherein the alignment feature comprises an outline of at least a portion of a perimeter of the electrode subassembly.

Aspect 46: The apparatus of aspect 44, wherein the electrode subassembly defines at least one opening therethrough, wherein the alignment feature comprises a corresponding marking on the skin contact subassembly that is viewable through each opening of the at least one opening through the electrode subassembly when the electrode subassembly is in the desired position relative to the skin contact subassembly.

Aspect 47: The apparatus of aspect 4, wherein the skin contact subassembly defines at least one opening therethrough, wherein the alignment feature comprises the at least one opening, wherein the electrode subassembly comprises a corresponding marking that is viewable through each opening of the at least one opening through the skin contact subassembly when the skin contact subassembly is in the desired position relative to the electrode subassembly.

Aspect 48: A method of using the apparatus of any one of the preceding aspects, the method comprising:

removing the skin contact subassembly from the electrically conductive polymer layer of the electrode subassembly.

Aspect 49: The method of aspect 48, further comprising positioning a new skin contact subassembly against the electrically conductive polymer layer of the electrode subassembly so that the new skin contact subassembly is removably coupled to the electrode subassembly.

Aspect 50: The method of aspect 49, further comprising cleaning the electrically conductive polymer layer of the electrode subassembly prior to positioning the new skin contact subassembly against the electrically conductive polymer layer of the electrode subassembly.

Aspect 51: The method of aspect 49, wherein the skin contact subassembly comprises at least one alignment feature that provides an indication of a desired position of the electrode subassembly relative to the skin contact subassembly, the method comprising using the at least one alignment feature to orient the electrode subassembly relative to the skin contact subassembly, or wherein the electrode subassembly comprises at least one alignment feature that provides an indication of a desired position of the skin contact subassembly relative to the electrode subassembly, the method comprising using the at least one alignment feature to orient the skin contact subassembly relative to the electrode subassembly.

Aspect 52: A kit comprising:

an electrode subassembly comprising:

at least one electrode element having a skin-facing side and a skin-facing surface; and an electrically conductive polymer layer on the skin-facing side of the at least one electrode element, wherein the electrically conductive polymer layer has a skin-facing surface which defines a skin-facing surface of the electrode subassembly; and a plurality of skin contact subassemblies, each skin contact subassembly configured to couple to the electrode subassembly as a removable unit, wherein each skin contact subassembly comprises a skin contact conductive adhesive or gel configured to contact skin of a subject, and, when the skin contact subassembly is disposed against the electrically conductive polymer layer of the electrode subassembly, the skin contact conductive adhesive or gel of the skin contact subassembly is configured to electrically couple to the at least one electrode element.

Aspect 53: The kit of aspect 52, wherein the skin contact subassemblies each comprise a three layer unit comprising the skin contact conductive adhesive or gel, a layer of anisotropic conductive material, and a second conductive adhesive or gel layer; wherein the anisotropic conductive material has a skin facing side with a skin facing surface and an opposing outwardly facing surface; and wherein the skin facing surface of the layer of anisotropic conductive material is in contact with the skin contact conductive adhesive or gel, and the outwardly facing surface of the layer of anisotropic conductive material is in contact with the second conductive adhesive or gel layer.

Aspect 54: The kit of aspect 53, wherein one or both of the skin contact conductive adhesive or gel and the second conductive adhesive or gel comprise:

a substrate layer;

a skin-facing substrate-associated conductive adhesive or gel layer; and an outwardly-facing substrate-associated conductive adhesive or gel layer.

Aspect 55: The kit of aspect 54, wherein the substrate layer has a continuous, uninterrupted structure, and wherein the substrate layer is electrically conductive.

Aspect 56: The kit of aspect 54, wherein the substrate layer has an at least partially open structure that is configured to permit contact of adhesive layers from either side of the substrate layer.

Aspect 57: The kit of aspect 56, wherein the substrate comprises a mesh or a scrim.

Aspect 58: The kit of any one of aspects 53-57, wherein the layer of anisotropic conductive material is or comprises a synthetic graphite.

Aspect 59: The kit of any one of aspects 53-57, wherein the layer of anisotropic conductive material is or comprises a layer of pyrolytic graphite, graphitized polymer film, or graphite foil made from compressed high purity exfoliated mineral graphite.

Aspect 60: The kit of any one of aspects 53-59, wherein the layer of anisotropic conductive material has a first thermal conductivity in a direction that is perpendicular to the skin facing surface, and wherein thermal conductivity of the sheet in directions that are parallel to the skin facing surface is more than two times higher than the first thermal conductivity.

Aspect 61: The kit of any one of aspects 53-60, wherein the layer of anisotropic conductive material has a first resistance in a direction that is perpendicular to the skin facing surface, and wherein resistance of the sheet in directions that are parallel to the skin facing surface is less than half of the first resistance.

Aspect 62: An apparatus comprising:

an electrode subassembly comprising:

at least one electrode element having a skin-facing side and a skin-facing surface; and a first conductive adhesive or gel on the skin-facing side of the at least one electrode element, wherein the first conductive adhesive or gel has a skin-facing surface which defines a skin-facing surface of the electrode subassembly; and a skin contact subassembly removably coupled to the electrode subassembly, wherein the skin contact subassembly comprises:

an electrically conductive polymer layer configured to removably couple to the electrode subassembly; and a skin contact conductive adhesive or gel configured to contact skin of a subject, wherein the skin contact conductive adhesive or gel is electrically coupled to the at least one electrode element when the conductive polymer layer of the skin contact subassembly is disposed against the skin-facing surface of the electrode subassembly.

Aspect 63: The apparatus of aspect 62, wherein the electrically conductive polymer layer of the skin contact subassembly comprises a rubber or elastomer.

Aspect 64: The apparatus of aspect 62, wherein the electrically conductive polymer layer of the skin contact subassembly comprises an adhesive or sealant.

Aspect 65: The apparatus of any one aspects 62-64, wherein the electrically conductive polymer layer of the skin contact subassembly comprises a silicone polymer.

Aspect 66: The apparatus of aspect 62, wherein the electrically conductive polymer layer of the skin contact subassembly is or comprises silicone rubber, silicone elastomer, natural rubber, poly cis-isoprene, polyisobutylene, polychloroprene, cis-polybutadiene, styrene-butadiene, styrene-acrylonitrile-butadiene, polyurethane, EPDM, EVA polymer, AEM polymer, fluoropolymer, or perfluoropolymer, or combinations thereof.

Aspect 67: The apparatus of any one of aspects 62-66, wherein the electrically conductive polymer layer of the skin contact subassembly comprises a composite material having conductive particles dispersed therethrough.

Aspect 68: The apparatus of aspect 67, wherein the conductive particles comprise carbon.

Aspect 69: The apparatus of aspect 68, wherein the conductive particles comprise one or more of: graphite powder, carbon flakes, carbon fibers, carbon granules, carbon nanotubes, carbon nanowires, carbon black powder, or carbon microcoils.

Aspect 70: The apparatus of aspect 69, wherein the conductive particles comprise metal.

Aspect 71: The apparatus of any one of aspects 62-70, wherein the electrode subassembly further comprises a dielectric layer between the at least one electrode element and the electrically conductive polymer layer of the skin contact subassembly.

Aspect 72: The apparatus of any one of the preceding aspects, wherein the electrode subassembly further comprises a dielectric layer between the at least one electrode element and the first conductive adhesive or gel of the electrode subassembly.

Aspect 73: The apparatus of aspect 71 or aspect 72, wherein the dielectric layer comprises a ceramic or dielectric polymer.

Aspect 74: The apparatus of aspect 73, wherein the dielectric layer comprises a dielectric polymer, and wherein the dielectric polymer has a dielectric constant greater than 10.

Aspect 75: The apparatus of any one of aspects 62-74, wherein the apparatus does not comprise an additional adhesive between the skin contact subassembly and the first conductive adhesive or gel of the electrode subassembly.

Aspect 76: The apparatus of any one of aspects 62-75, wherein the first conductive adhesive or gel of the electrode subassembly and the skin contact subassembly are removably coupled by a physical, non-chemical adhesion.

Aspect 77: The apparatus of any one of aspects 62-76, wherein the first conductive adhesive or gel of the electrode subassembly and the skin contact subassembly are removably coupled by a Van der Waals attractive force.

Aspect 78: The apparatus of any one of aspects 62-77, wherein the electrically conductive polymer layer of the skin contact subassembly has a smooth surface that removably couples to the electrode subassembly.

Aspect 79: The apparatus of any one of aspects 62-78, wherein the electrically conductive polymer layer of the skin contact subassembly is not tacky.

Aspect 80: The apparatus of any one of aspects 62-79, wherein the skin contact subassembly further comprises a layer of anisotropic conductive material having a skin-facing side with a skin-facing surface and an opposing outwardly facing surface, wherein the layer of anisotropic conductive material is disposed in contact with the skin contact conductive adhesive or gel.

Aspect 81: The apparatus of any one of aspects 62-80, wherein the skin contact conductive adhesive or gel comprises a conductive adhesive composite.

Aspect 82: The apparatus of aspects 81, wherein the conductive adhesive composite comprises conductive particles dispersed therethrough.

Aspect 83: The apparatus of aspect 82, wherein the conductive particles comprise carbon.

Aspect 86: The apparatus of aspect 83, wherein the conductive particles comprise one or more of: graphite powder, carbon flakes, carbon fibers, carbon granules, carbon nanotubes, carbon nanowires, carbon black powder, or carbon microcoils.

Aspect 85: The apparatus of aspect 82, wherein the conductive particles comprise metal.

Aspect 86: The apparatus of any one of the preceding aspects, wherein the skin contact subassembly further comprises a layer of anisotropic conductive material.

Aspect 87: The apparatus of any one of aspects 62-86, wherein the electrode subassembly comprises a three layer unit comprising the first conductive adhesive or gel, a layer of anisotropic conductive material, and an upper conductive adhesive or gel, wherein the layer of anisotropic conductive material has a skin facing side with a skin facing surface and an opposing outwardly facing surface, and wherein the skin facing surface of the layer of anisotropic conductive material is in contact with the first conductive adhesive or gel, and the outwardly facing surface of the layer of anisotropic conductive material is in contact with the upper conductive adhesive or gel.

Aspect 88: The apparatus of aspect 87, wherein one or both of the first conductive adhesive or gel and the upper conductive adhesive or gel comprise:

- a substrate layer;
- a skin-facing substrate-associated conductive adhesive or gel layer; and
- an outwardly-facing substrate-associated conductive adhesive or gel layer.

Aspect 89: The apparatus of aspect 88, wherein the substrate layer has a continuous, uninterrupted structure, and wherein the substrate layer is electrically conductive.

Aspect 90: The apparatus of aspect 88, wherein the substrate layer has an at least partially open structure that is configured to permit contact of adhesive layers from either side of the substrate layer.

Aspect 91: The apparatus of aspect 90, wherein the substrate comprises a mesh or a scrim.

Aspect 92: The apparatus of aspect 91, wherein one or more of the skin contact conductive adhesive or gel, the skin-facing substrate-associated conductive adhesive or gel layer or the outwardly-facing substrate-associated conductive adhesive or gel layer is a conductive adhesive composite.

Aspect 93: The apparatus of aspect 92, wherein the conductive adhesive composite comprises conductive particles dispersed therethrough.

Aspect 94: The apparatus of aspect 93, wherein the conductive particles comprise carbon.

Aspect 95: The apparatus of aspect 94, wherein the conductive particles comprise one or more of: graphite powder, carbon flakes, carbon fibers, carbon granules, carbon nanotubes, carbon nanowires, carbon black powder, or carbon microcoils.

Aspect 96: The apparatus of aspect 93, wherein the conductive particles comprise metal.

Aspect 97: The apparatus of any one of aspects 62-96, wherein the skin contact subassembly comprises acrylic adhesive.

Aspect 98: The apparatus of aspect 96 or aspect 97, wherein the layer of anisotropic conductive material is or comprises a synthetic graphite.

Aspect 99: The apparatus of aspect 80 or aspect 87, wherein the layer of anisotropic conductive material is or comprises a layer of pyrolytic graphite, graphitized polymer film, or graphite foil made from compressed high purity exfoliated mineral graphite.

Aspect 100: The apparatus of aspect 80 or aspect 87, wherein the layer of anisotropic conductive material has a first thermal conductivity in a direction that is perpendicular to the skin facing surface, and wherein thermal conductivity of the sheet in directions that are parallel to the skin facing surface is more than two times higher than the first thermal conductivity.

Aspect 101: The apparatus of aspect 80 or aspect 87, wherein the layer of anisotropic conductive material has a first resistance in a direction that is perpendicular to the skin facing surface, and wherein resistance of the sheet in directions that are parallel to the skin facing surface is less than half of the first resistance.

Aspect 102: The apparatus of any one of aspects 62-101, wherein the electrode subassembly has an operative conductive area, wherein the skin contact subassembly has an areal footprint that overlies an entirety of the operative conductive area.

Aspect 103: The apparatus of any one of aspects 62-102, wherein the electrode subassembly has an operative conductive area, wherein the skin contact subassembly has an areal footprint that overlies an entirety of the operative conductive area, and wherein the skin contact subassembly comprises at least one alignment feature that provides an indication of a desired position of the electrode subassembly relative to the skin contact subassembly.

Aspect 104: The apparatus of aspect 103, wherein the alignment feature comprises an outline of at least a portion of a perimeter of the skin contact subassembly.

Aspect 105: The apparatus of aspect 103, wherein the electrode subassembly defines at least one opening therethrough, wherein the alignment feature comprises a corresponding marking on the skin contact subassembly that is viewable through each opening of the at least one opening through the electrode subassembly when the electrode subassembly is in the desired position relative to the skin contact subassembly.

Aspect 106: The apparatus of aspect 103, wherein the skin contact subassembly defines at least one opening therethrough, wherein the alignment feature comprises the at least one opening, wherein the electrode subassembly comprises a corresponding marking that is viewable through each opening of the at least one opening through the skin contact subassembly when the skin contact subassembly is in the desired position relative to the electrode subassembly.

Aspect 107: A method of using the apparatus of any one of aspects 62-106, the method comprising:

removing the skin contact subassembly from the first conductive adhesive or gel of the electrode subassembly.

Aspect 108: The method of aspect 107, further comprising positioning a new skin contact subassembly against the first conductive adhesive or gel of the electrode subassembly so that the new skin contact subassembly is removably coupled to the electrode subassembly.

Aspect 109: The method of aspect 108, further comprising cleaning the first conductive adhesive or gel of the electrode subassembly prior to positioning the new skin contact subassembly against the first conductive adhesive or gel of the electrode subassembly.

Aspect 110: The method of aspect 108, wherein the electrode subassembly comprises at least one alignment feature that provides an indication of a desired position of the skin contact subassembly relative to the electrode subassembly, the method comprising using the at least one alignment feature to orient the skin contact subassembly relative to the electrode subassembly.

Aspect 111: A kit comprising:

an electrode subassembly comprising:

at least one electrode element having a skin-facing side and a skin-facing surface; and a first conductive adhesive or gel on the skin-facing side of the at least one electrode element, wherein the first conductive adhesive or gel has a skin-facing surface which defines a skin-facing surface of the electrode subassembly; and a plurality of skin contact subassemblies, wherein each skin contact subassembly is configured to couple to the electrode subassembly as a removable unit, wherein each skin contact subassembly comprises:

an electrically conductive polymer layer configured to be removably coupled to the skin-facing surface of the electrode subassembly; and a skin contact conductive adhesive or gel configured to contact skin of a subject, wherein, when the electrically conductive polymer layer of the skin contact subassembly is disposed against the skin-facing surface of the electrode subassembly, the skin contact conductive adhesive or gel of the skin contact subassembly is electrically coupled to the at least one electrode element.

Aspect 112: The kit of aspect 111, wherein the electrode subassembly comprises a three layer unit comprising the first conductive adhesive or gel, a layer of anisotropic conductive material, and an upper conductive adhesive or gel, wherein the layer of anisotropic conductive material has a skin facing side with a skin facing surface and an opposing outwardly facing surface, and wherein the skin facing surface of the layer of anisotropic conductive material is in contact with the first conductive adhesive or gel, and the outwardly facing surface of the layer of anisotropic conductive material is in contact with the upper conductive adhesive or gel.

Aspect 113: The kit of aspect 112, wherein one or both of the first conductive adhesive or gel or the upper conductive adhesive or gel comprise:

a substrate layer;

a skin-facing substrate-associated conductive adhesive or gel layer; and an outwardly-facing substrate-associated conductive adhesive or gel layer.

Aspect 114: The kit of aspect 113, wherein the substrate layer has a continuous, uninterrupted structure, and wherein the substrate layer is electrically conductive.

Aspect 115: The kit of aspect 113, wherein the substrate layer has an at least partially open structure that is configured to permit contact of adhesive layers from either side of the substrate layer.

Aspect 116: The kit of aspect 115, wherein the substrate comprises a mesh or a scrim.

Aspect 117: The kit of any one of aspects 111-116, wherein the layer of anisotropic conductive material is or comprises a synthetic graphite.

Aspect 118: The kit of any one of aspects 111-117, wherein the layer of anisotropic conductive material is or comprises a layer of pyrolytic graphite, graphitized polymer film, or graphite foil made from compressed high purity exfoliated mineral graphite.

Aspect 119: The kit of any one of aspects 112-118, wherein the layer of anisotropic conductive material has a first thermal conductivity in a direction that is perpendicular to the skin facing surface, and wherein thermal conductivity of the sheet in directions that are parallel to the skin facing surface is more than two times higher than the first thermal conductivity.

Aspect 120: The kit of any one of aspects 12-119, wherein the layer of anisotropic conductive material has a first resistance in a direction that is perpendicular to the skin facing surface, and wherein resistance of the sheet in directions that are parallel to the skin facing surface is less than half of the first resistance.

Aspect 121: An apparatus comprising:

an electrode subassembly comprising:

at least one electrode element having a skin-facing side and a skin-facing surface; and a skin contact subassembly comprising a skin contact conductive adhesive or gel configured to contact skin of a subject, wherein one of the electrode subassembly or the skin contact subassembly comprises an electrically conductive polymer layer, wherein the other of the electrode subassembly or the skin contact subassembly comprises a second conductive adhesive or gel, wherein the electrically conductive polymer layer is disposed against, and removably coupled to, the second conductive adhesive or gel, thereby removably coupling the electrode subassembly to the skin contact subassembly so that the skin contact conductive adhesive or gel is electrically coupled to the at least one electrode element.

Aspect 122: An apparatus comprising:

an electrode subassembly having a skin-facing side and a skin-facing surface, and comprising at least one electrode element having a skin-facing side and a skin-facing surface; and a skin contact subassembly comprising a skin contact conductive adhesive or gel configured to contact skin of a subject, wherein one of the electrode subassembly or the skin contact subassembly comprises an electrically conductive polymer layer, wherein the other of the electrode subassembly or the skin contact subassembly comprises a conductive adhesive or gel layer, and wherein the skin contact subassembly is removably coupled to the electrode subassembly by adhesion between the electrically conductive polymer layer and the conductive adhesive or gel layer, and wherein the skin contact conductive adhesive or gel is electrically coupled to the at least one electrode element when the skin contact subassembly is disposed against the skin-facing surface of the electrode subassembly.

Aspect 123: The apparatus of aspect 122, wherein the electrode subassembly comprises the electrically conductive polymer layer, wherein the electrically conductive polymer layer is a non-adhesive electrically conductive polymer layer positioned on the skin-facing side of the at least one electrode element, wherein the non-adhesive electrically conductive polymer layer has a skin-facing surface which defines a skin-facing surface of the electrode subassembly.

Aspect 124: The apparatus of aspect 122, wherein the electrically conductive polymer layer is adhered to the skin contact conductive adhesive or gel of the skin contact subassembly.

Aspect 125: The apparatus of aspect 123, wherein the skin contact subassembly comprises at least one additional layer of conductive adhesive or gel, wherein the non-adhesive electrically conductive polymer layer of the electrode subassembly is removably adhered to the at least one additional layer of conductive adhesive or gel of the skin contact subassembly.

Aspect 126: The apparatus of aspect 123, wherein the non-adhesive electrically conductive polymer layer is or comprises silicone rubber or silicone elastomer.

Aspect 127: The apparatus of any one of aspects 122-126, wherein the electrically conductive polymer layer is or comprises silicone rubber, silicone elastomer, natural rubber, poly cis-isoprene, polyisobutylene, polychloroprene, cis-polybutadiene, styrene-butadiene, styrene-acrylonitrile-butadiene, polyurethane, EPDM, EVA polymer, AEM polymer, fluoropolymer, perfluoropolymer, polyetherimide, polyetherketone, polyethersulfone, polyether ether ketone, or polyaryl ether ketone, or combinations thereof.

Aspect 128: The apparatus of any one of aspects 122-126, wherein the electrically conductive polymer layer is or comprises silicone rubber, silicone elastomer, natural rubber, poly cis-isoprene, polyisobutylene, polychloroprene, cis-polybutadiene, styrene-butadiene, styrene-acrylonitrile-butadiene, polyurethane, EPDM, EVA polymer, AEM polymer, fluoropolymer, or perfluoropolymer, or combinations thereof, Aspect 129: The apparatus of any one of aspects 122-127, wherein the electrically conductive polymer layer comprises a composite material having conductive particles dispersed therethrough.

Aspect 130: The apparatus of aspects 129, wherein the conductive particles comprise carbon particles.

Aspect 131: The apparatus of any one of aspects 123-130, wherein the non-adhesive electrically conductive polymer layer of the electrode subassembly has an outwardly facing surface that faces the at least one electrode element, the electrode subassembly further comprising an electrode subassembly conductive adhesive or gel layer disposed against the outwardly facing surface of the non-adhesive electrically conductive polymer layer.

Aspect 132: The apparatus of any one of aspects 123-131, wherein the electrode subassembly further comprises a dielectric layer between the at least one electrode element and the non-adhesive electrically conductive polymer layer of the electrode subassembly.

Aspect 133: The apparatus of any one of aspects 122-132, wherein the electrode subassembly has an operative conductive area, and wherein the skin contact subassembly has an areal footprint that overlies an entirety of the operative conductive area.

Aspect 134: The apparatus of any one of aspects 122-133, wherein either the skin contact subassembly or the electrode subassembly, or both, further comprises a layer of anisotropic conductive material.

Aspect 135: The apparatus of aspect 134, wherein the layer of anisotropic conductive material is sandwiched between, and in contact with, respective layers of conductive adhesive or gel on each respective surface of the layer of anisotropic conductive material.

Aspect 136: The apparatus of aspect 134, wherein the skin contact subassembly comprises the layer of anisotropic conductive material, wherein the layer of anisotropic conductive material has a skin-facing side with a skin-facing surface and an opposing outwardly facing surface, wherein the layer of anisotropic conductive material is disposed in contact with the skin contact conductive adhesive or gel, and wherein the at least one electrode element is in electrical contact with the outwardly facing surface of the layer of anisotropic conductive material when the electrode subassembly is in contact with the skin contact subassembly.

Aspect 137: The apparatus of any one of aspects 122-136, wherein the skin contact subassembly comprises a three layer unit comprising a layer of anisotropic conductive material having a skin facing side with a skin facing surface and an opposing outwardly facing surface; and wherein the skin facing surface of the layer of anisotropic conductive material is in contact with the skin contact conductive adhesive or gel, and the outwardly facing surface of the layer of anisotropic conductive material is in contact with a second conductive adhesive or gel layer.

Aspect 138: The apparatus of any one of aspects 133-137, wherein the layer of anisotropic conductive material is or comprises a synthetic graphite.

Aspect 139: The apparatus of any one of aspects 123-138, wherein the non-adhesive electrically conductive polymer layer of the electrode subassembly and the skin contact subassembly are removably coupled by a Van der Waals attractive force.

Aspect 140: The apparatus of any one of aspects 122-139, wherein an attractive force between the electrode subassembly and the skin contact subassembly is supplemented by an added attractive force around a perimeter of the electrode subassembly and the skin contact subassembly, the added attractive force provided by:

i) Positioning one of a hook or loop material on the electrode subassembly and the other of the hook or loop material on the skin contact subassembly; or ii) positioning one of a pair of magnets on the electrode subassembly and the other of the pair of magnets on the skin contact subassembly; or iii) adhering a perimeter region of the electrode subassembly to the skin contact subassembly, or vice-versa, using an adhesive or adhesive tape; or iv) joining a perimeter region of the electrode subassembly to the skin contact subassembly, or vice-versa, using a button and buttonhole fastener or a snap-fastener; or v) combinations thereof.

Aspect 141: The apparatus of any one of aspects 123-140, wherein the apparatus is free of a layer of electrode subassembly conductive adhesive or gel between the at least one electrode and the non-adhesive electrically conductive polymer layer.

Aspect 142: The apparatus of any one of aspects 122-141, wherein the electrically conductive polymer layer comprises a conductive adhesive or gel or a conductive sealant.

Aspect 143: The apparatus of aspect 122, wherein the skin contact subassembly comprises the electrically conductive polymer layer, wherein the electrically conductive polymer layer is a non-adhesive electrically conductive polymer layer, wherein the electrode subassembly comprises at least one layer of electrode subassembly conductive adhesive or gel, and wherein the skin contact subassembly is removably coupled to the electrode subassembly by adhesion between the electrically conductive polymer layer of the skin contact subassembly and the at least one layer of electrode subassembly conductive adhesive or gel.

Aspect 144: The apparatus of aspect 143, wherein the skin contact subassembly comprises a skin contact adhesive or gel which defines a skin-facing surface of the skin contact subassembly, and wherein either the skin contact subassembly or the electrode subassembly, or both, further comprises a layer of anisotropic conductive material Aspect 145: The apparatus of any one of aspects 1-9, 16-47, or 121-144, wherein the apparatus is free of an additional layer of electrode subassembly conductive adhesive or gel between the at least one electrode and the electrically conductive polymer layer.

Aspect 146: The apparatus of aspect 145, wherein the electrode subassembly comprises a dielectric layer between the at least one electrode and the electrically conductive polymer layer, wherein the electrically conductive polymer layer of the skin contact subassembly is deposited on the dielectric layer.

Aspect 147: The apparatus of aspect 146, wherein the skin contact subassembly comprises the electrically conductive polymer layer, wherein the electrically conductive polymer layer is a non-adhesive electrically conductive polymer layer and the electrode subassembly comprises at least one layer of electrode subassembly conductive adhesive or gel, and wherein the skin contact subassembly is removably coupled to the electrode subassembly by adhesion between the electrically conductive polymer layer of the skin contact subassembly and the at least one layer of electrode subassembly conductive adhesive or gel.

Aspect 148: The apparatus of aspect 147, wherein the skin contact subassembly comprises a skin contact adhesive or gel which defines a skin-facing surface of the skin contact subassembly, and wherein either the skin contact subassembly or the electrode subassembly, or both, further comprises a layer of anisotropic conductive material.

Aspect 149: A kit comprising:

an electrode subassembly comprising:

at least one electrode element having a skin-facing side and a skin-facing surface; and a non-adhesive electrically conductive polymer layer on the skin-facing side of the at least one electrode element, wherein the non-adhesive electrically conductive polymer layer has a skin-facing surface which defines a skin-facing surface of the electrode subassembly; and a plurality of skin contact subassemblies, each skin contact subassembly configured to couple to the electrode subassembly as a removable unit, wherein each skin contact subassembly comprises a skin contact conductive adhesive or gel configured to contact skin of a subject, and, when the skin contact subassembly is disposed against the non-adhesive electrically conductive polymer layer of the electrode subassembly, the skin contact conductive adhesive or gel of the skin contact subassembly is configured to electrically couple to the at least one electrode element.

Aspect 150: A method comprising:

using an apparatus as in any one of aspects 121-148; and removing the skin contact subassembly from the electrode subassembly.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof. For example, various combinations of layer arrangements are disclosed with reference to the illustrated embodiments. Logical combinations and omissions of the different layers are contemplated. As another example, various skin contact subassemblies are illustrated in combination with different electrode subassemblies. It should be understood that the electrode subassemblies and skin contact subassemblies can logically be interchanged within the spirit and scope of the present disclosure. For example, FIG. 2 shows an embodiment in which the skin contact subassembly includes a layer of anisotropic material, while the electrode subassembly does not; and FIG. 15 shows an embodiment in which the electrode subassembly includes a layer of anisotropic material, while the skin contact subassembly does not. Further, FIG. 4 shows an embodiment in which both the electrode subassembly and the skin contact subassembly each comprise a layer of anisotropic material.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

What is claimed is:

1. An apparatus comprising:

an electrode subassembly having a skin-facing side and a skin-facing surface, and comprising at least one electrode element having a skin-facing side and a skin-facing surface; and a skin contact subassembly comprising:

a skin contact conductive adhesive or skin contact conductive gel configured to contact skin of a subject; and a layer of anisotropic conductive material, wherein the layer of anisotropic conductive material has a skin-facing side with a skin-facing surface and an opposing outwardly facing surface, wherein the layer of anisotropic conductive material is disposed in contact with the skin contact conductive adhesive or skin contact conductive gel, and wherein the at least one electrode element is in electrical contact with the outwardly facing surface of the layer of anisotropic conductive material;

wherein one of the electrode subassembly or the skin contact subassembly comprises an electrically conductive polymer layer, wherein the other of the electrode subassembly or the skin contact subassembly comprises a layer of conductive adhesive or conductive gel, and wherein the skin contact subassembly is removably coupled to the electrode subassembly by adhesion between the electrically conductive polymer layer and the layer of conductive adhesive or conductive gel, and wherein the skin contact conductive adhesive or skin contact conductive gel is electrically coupled to the at least one electrode element.

2. The apparatus of claim 1, wherein the electrode subassembly comprises the electrically conductive polymer layer, wherein the electrically conductive polymer layer is a non-adhesive electrically conductive polymer layer positioned on the skin-facing side of the at least one electrode element, wherein the non-adhesive electrically conductive polymer layer has a skin-facing surface which defines a skin-facing surface of the electrode subassembly.

3. The apparatus of claim 2, wherein the skin contact subassembly comprises at least one additional layer of conductive adhesive or conductive gel, wherein the non-adhesive electrically conductive polymer layer of the electrode subassembly is removably adhered to the at least one additional layer of conductive adhesive or conductive gel of the skin contact subassembly.

4. The apparatus of claim 2, wherein the non-adhesive electrically conductive polymer layer is or comprises silicone rubber or silicone elastomer.

5. The apparatus of claim 2, wherein the non-adhesive electrically conductive polymer layer of the electrode subassembly has an outwardly facing surface that faces the at least one electrode element, the electrode subassembly further comprising an electrode subassembly conductive adhesive layer or an electrode subassembly conductive gel layer disposed against the outwardly facing surface of the non-adhesive electrically conductive polymer layer.

6. The apparatus of claim 2, wherein the electrode subassembly further comprises a dielectric layer between the at least one electrode element and the non-adhesive electrically conductive polymer layer of the electrode subassembly.

7. The apparatus of claim 2, wherein the skin contact subassembly comprises a three layer unit, the three layer unit comprising:

the layer of anisotropic conductive material;

the skin contact conductive adhesive or skin contact conductive gel; and a second layer of conductive adhesive or conductive gel;

wherein the skin facing surface of the layer of anisotropic conductive material is in contact with the skin contact conductive adhesive or skin contact conductive gel, and the outwardly facing surface of the layer of anisotropic conductive material is in contact with the second layer of conductive adhesive or conductive gel.

8. The apparatus of claim 2, wherein the non-adhesive electrically conductive polymer layer of the electrode subassembly and the skin contact subassembly are removably coupled by a Van der Waals attractive force.

9. The apparatus of claim 2, wherein the apparatus is free of a layer of electrode subassembly conductive adhesive or conductive gel between the at least one electrode and the non-adhesive electrically conductive polymer layer.

10. The apparatus of claim 1, wherein the electrically conductive polymer layer is or comprises silicone rubber, silicone elastomer, natural rubber, poly cis-isoprene, polyisobutylene, polychloroprene, cis-polybutadiene, styrene-butadiene, styrene-acrylonitrile-butadiene, polyurethane, EPDM, EVA polymer, AEM polymer, fluoropolymer, perfluoropolymer, polyetherimide, polyetherketone, polyethersulfone, polyether ether ketone, or polyaryl ether ketone, or combinations thereof.

11. The apparatus of claim 1, wherein the electrically conductive polymer layer comprises a composite material having conductive particles dispersed therethrough.

12. The apparatus of claim 11, wherein the conductive particles comprise carbon particles.

13. The apparatus of claim 1, wherein the electrode subassembly has an operative conductive area, and wherein the skin contact subassembly has an areal footprint that overlies an entirety of the operative conductive area.

14. The apparatus of claim 1, wherein the layer of anisotropic conductive material of the skin contact subassembly is a first layer of anisotropic conductive material, and wherein the electrode subassembly further comprises a second layer of anisotropic conductive material.

15. The apparatus of claim 1, wherein the layer of conductive adhesive or conductive gel of the skin contact subassembly is a first layer of conductive adhesive or conductive gel, wherein the skin contact subassembly further comprises a second layer of conductive adhesive or conductive gel, wherein the layer of anisotropic conductive material is sandwiched between the first layer of conductive adhesive or conductive gel and the second layer of conductive adhesive or conductive gel, wherein the first layer of conductive adhesive or conductive gel is in contact with the skin facing surface of the layer of anisotropic conductive material, and wherein the second layer of conductive adhesive or conductive gel is in contact with the opposed outwardly facing surface of the layer of anisotropic conductive material.

16. The apparatus of claim 1, wherein the layer of anisotropic conductive material is or comprises graphite.

17. The apparatus of claim 1, wherein an attractive force between the electrode subassembly and the skin contact subassembly is supplemented by an added attractive force around a perimeter of the electrode subassembly and the skin contact subassembly, the added attractive force provided by one or more of:

i) one of a hook or loop material positioned on the electrode subassembly and the other of the hook or loop material positioned on the skin contact subassembly; or ii) one of a pair of magnets on the electrode subassembly positioned and the other of the pair of magnets positioned on the skin contact subassembly; or iii) a perimeter region of the electrode subassembly adhered to the skin contact subassembly, or vice-versa, using an adhesive or adhesive tape; or iv) a perimeter region of the electrode subassembly joined to the skin contact subassembly, or vice-versa, using a button and buttonhole fastener or a snap-fastener.

18. The apparatus of claim 1, wherein the electrically conductive polymer layer comprises a conductive adhesive or conductive gel or a conductive sealant.

19. The apparatus of claim 1, wherein the skin contact subassembly comprises the electrically conductive polymer layer, wherein the electrically conductive polymer layer is a non-adhesive electrically conductive polymer layer, wherein the electrode subassembly comprises at least one layer of electrode subassembly conductive adhesive or conductive gel, and wherein the skin contact subassembly is removably coupled to the electrode subassembly by adhesion between the electrically conductive polymer layer of the skin contact subassembly and the at least one layer of electrode subassembly conductive adhesive or conductive gel.

20. A method comprising:

using the apparatus as in claim 1; and removing the skin contact subassembly from the electrode subassembly.

* * * * *